US012648718B2

(12) United States Patent
Al-Ali et al.

(10) Patent No.: US 12,648,718 B2
(45) Date of Patent: Jun. 9, 2026

(54) REGIONAL OXIMETRY SENSOR

(71) Applicant: MASIMO CORPORATION, Irvine, CA (US)

(72) Inventors: Ammar Al-Ali, San Juan Capistrano, CA (US); Kevin Forrest, Rancho Santa Margarita, CA (US); Yassir Abdul-Hafiz, Irvine, CA (US); Walter M. Weber, Laguna Hills, CA (US); Pete Mangosing, Santa Ana, CA (US); Sujin Hwang, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 203 days.

(21) Appl. No.: 18/364,258

(22) Filed: Aug. 2, 2023

(65) Prior Publication Data

US 2024/0023840 A1 Jan. 25, 2024

Related U.S. Application Data

(63) Continuation of application No. 16/745,894, filed on Jan. 17, 2020, now Pat. No. 11,751,780, which is a continuation of application No. 15/891,910, filed on Feb. 8, 2018, now Pat. No. 10,617,335, which is a continuation of application No. 14/507,620, filed on Oct. 6, 2014, now abandoned.

(Continued)

(51) Int. Cl.
*A61B 5/1455* (2006.01)
*A61B 5/00* (2006.01)
(Continued)

(52) U.S. Cl.
CPC ........ *A61B 5/14542* (2013.01); *A61B 5/1455* (2013.01); *A61B 5/14552* (2013.01);
(Continued)

(58) Field of Classification Search
CPC .............. A61B 5/1455; A61B 5/14532; A61B 5/14552; A61B 5/14551
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| (Continued) | | | |

FOREIGN PATENT DOCUMENTS

| | | |
|---|---|---|
| CN | 1805767 | 7/2006 |
| JP | H02-163634 | 6/1990 |
| (Continued) | | |

OTHER PUBLICATIONS

US 2022/0192529 A1, 06/2022, Al-Ali et al. (withdrawn)
(Continued)

*Primary Examiner* — Marjan Fardanesh
(74) *Attorney, Agent, or Firm* — Knobbe, Martens, Olson & Bear, LLP

(57) ABSTRACT

A regional oximetry sensor can have a sensor head configured to secure to skin of a user and a stem extending from the sensor head. The sensor head can include an emitter configured to transmit optical radiation into the skin and at least one detector configured to receive the optical radiation after attenuation by blood flow within the skin. The stem can be configured to transmit electrical signals from the sensor head to a cable. A plurality of notches can extend from a perimeter of the sensor head towards an interior thereof. The plurality of notches can form a plurality of independently flexible cutouts in the sensor head configured to allow for movement of at least a portion of the skin of the user underlying the sensor head when the regional oximetry sensor is in use.

20 Claims, 13 Drawing Sheets

Related U.S. Application Data

(60) Provisional application No. 62/012,170, filed on Jun. 13, 2014, provisional application No. 61/887,878, filed on Oct. 7, 2013, provisional application No. 61/887,856, filed on Oct. 7, 2013, provisional application No. 61/887,883, filed on Oct. 7, 2013.

(51) Int. Cl.
| | |
|---|---|
| *A61B 5/145* | (2006.01) |
| *H01R 13/52* | (2006.01) |

(52) U.S. Cl.
CPC ........ *A61B 5/14553* (2013.01); *A61B 5/6833* (2013.01); *A61B 5/7275* (2013.01); *A61B 5/742* (2013.01); *A61B 5/746* (2013.01); *A61B 5/14551* (2013.01); *A61B 5/14557* (2013.01); *A61B 2562/22* (2013.01); *A61B 2562/222* (2013.01); *A61B 2562/225* (2013.01); *A61B 2562/227* (2013.01); *A61B 2562/228* (2013.01); *H01R 13/5224* (2013.01); *H01R 2201/12* (2013.01)

(56) References Cited

U.S. PATENT DOCUMENTS

| | | | |
|---|---|---|---|
| 4,974,591 A * | 12/1990 | Awazu ............... | A61B 5/14552 |
| | | | 600/479 |
| 5,041,187 A | 8/1991 | Hink et al. | |
| 5,069,213 A | 12/1991 | Hink et al. | |
| 5,069,214 A | 12/1991 | Samaras et al. | |
| 5,163,438 A | 11/1992 | Gordon et al. | |
| 5,237,994 A | 8/1993 | Goldberger | |
| 5,305,746 A | 4/1994 | Fendrock | |
| 5,319,355 A | 6/1994 | Russek | |
| 5,337,744 A | 8/1994 | Branigan | |
| 5,341,805 A | 8/1994 | Stavridi et al. | |
| 5,348,004 A | 9/1994 | Hollub | |
| D353,195 S | 12/1994 | Savage et al. | |
| D353,196 S | 12/1994 | Savage et al. | |
| 5,377,676 A | 1/1995 | Vari et al. | |
| D359,546 S | 6/1995 | Savage et al. | |
| 5,431,170 A | 7/1995 | Mathews | |
| 5,436,499 A | 7/1995 | Namavar et al. | |
| D361,840 S | 8/1995 | Savage et al. | |
| D362,063 S | 9/1995 | Savage et al. | |
| 5,452,717 A | 9/1995 | Branigan et al. | |
| D363,120 S | 10/1995 | Savage et al. | |
| 5,456,252 A | 10/1995 | Vari et al. | |
| 5,479,934 A | 1/1996 | Imran | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,534,851 A | 7/1996 | Russek | |
| 5,561,275 A | 10/1996 | Savage et al. | |
| 5,590,649 A | 1/1997 | Caro et al. | |
| 5,602,924 A | 2/1997 | Durand et al. | |
| 5,632,272 A | 5/1997 | Diab et al. | |
| 5,632,273 A | 5/1997 | Suzuki | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,671,914 A | 9/1997 | Kalkhoran et al. | |
| 5,685,299 A | 11/1997 | Diab et al. | |
| 5,726,440 A | 3/1998 | Kalkhoran et al. | |
| D393,830 S | 4/1998 | Tobler et al. | |
| 5,743,262 A | 4/1998 | Lepper, Jr. et al. | |
| 5,747,806 A | 5/1998 | Khalil et al. | |
| 5,750,994 A | 5/1998 | Schlager | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,987,343 A | 11/1999 | Kinast | |
| 5,995,855 A | 11/1999 | Kiani et al. | |
| 5,997,343 A | 12/1999 | Mills et al. | |
| 6,002,952 A | 12/1999 | Diab et al. | |
| 6,010,937 A | 1/2000 | Karam et al. | |
| 6,011,986 A | 1/2000 | Diab et al. | |
| 6,027,452 A | 2/2000 | Flaherty et al. | |
| 6,036,642 A | 3/2000 | Diab et al. | |
| 6,040,578 A | 3/2000 | Malin et al. | |
| 6,045,509 A | 4/2000 | Caro et al. | |
| 6,066,204 A | 5/2000 | Haven | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,115,673 A | 9/2000 | Malin et al. | |
| 6,124,597 A | 9/2000 | Shehada et al. | |
| 6,128,521 A | 10/2000 | Marro et al. | |
| 6,129,675 A | 10/2000 | Jay | |
| 6,144,868 A | 11/2000 | Parker | |
| 6,151,516 A | 11/2000 | Kiani-Azarbayjany et al. | |
| 6,152,754 A | 11/2000 | Gerhardt et al. | |
| 6,157,850 A | 12/2000 | Diab et al. | |
| 6,165,005 A | 12/2000 | Mills et al. | |
| 6,184,521 B1 | 2/2001 | Coffin, IV et al. | |
| 6,206,830 B1 | 3/2001 | Diab et al. | |
| 6,229,856 B1 | 5/2001 | Diab et al. | |
| 6,232,609 B1 | 5/2001 | Snyder et al. | |
| 6,236,872 B1 | 5/2001 | Diab et al. | |
| 6,241,683 B1 | 6/2001 | Macklem et al. | |
| 6,253,097 B1 | 6/2001 | Aronow et al. | |
| 6,255,708 B1 | 7/2001 | Sudharsanan et al. | |
| 6,256,523 B1 | 7/2001 | Diab et al. | |
| 6,263,222 B1 | 7/2001 | Diab et al. | |
| 6,278,522 B1 | 8/2001 | Lepper, Jr. et al. | |
| 6,280,213 B1 | 8/2001 | Tobler et al. | |
| 6,280,381 B1 | 8/2001 | Malin et al. | |
| 6,285,896 B1 | 9/2001 | Tobler et al. | |
| 6,298,255 B1 | 10/2001 | Cordero et al. | |
| 6,301,493 B1 | 10/2001 | Marro et al. | |
| 6,308,089 B1 | 10/2001 | von der Ruhr et al. | |
| 6,317,627 B1 | 11/2001 | Ennen et al. | |
| 6,321,100 B1 | 11/2001 | Parker | |
| 6,325,761 B1 | 12/2001 | Jay | |
| 6,334,065 B1 | 12/2001 | Al-Ali et al. | |
| 6,343,224 B1 | 1/2002 | Parker | |
| 6,349,228 B1 | 2/2002 | Kiani et al. | |
| 6,360,114 B1 | 3/2002 | Diab et al. | |
| 6,368,283 B1 | 4/2002 | Xu et al. | |
| 6,371,921 B1 | 4/2002 | Caro et al. | |
| 6,377,829 B1 | 4/2002 | Al-Ali | |
| 6,388,240 B2 | 5/2002 | Schulz et al. | |
| 6,397,091 B2 | 5/2002 | Diab et al. | |
| 6,411,373 B1 | 6/2002 | Garside et al. | |
| 6,415,167 B1 | 7/2002 | Blank et al. | |
| 6,430,437 B1 | 8/2002 | Marro | |
| 6,430,525 B1 | 8/2002 | Weber et al. | |
| 6,434,410 B1 | 8/2002 | Cordero et al. | |
| 6,463,311 B1 | 10/2002 | Diab | |
| 6,470,199 B1 | 10/2002 | Kopotic et al. | |
| 6,487,429 B2 | 11/2002 | Hockersmith et al. | |
| 6,501,975 B2 | 12/2002 | Diab et al. | |
| 6,505,059 B1 | 1/2003 | Kollias et al. | |
| 6,515,273 B2 | 2/2003 | Al-Ali | |
| 6,519,487 B1 | 2/2003 | Parker | |
| 6,525,386 B1 | 2/2003 | Mills et al. | |
| 6,526,300 B1 | 2/2003 | Kiani et al. | |
| 6,534,012 B1 | 3/2003 | Hazen et al. | |

(56) References Cited

U.S. PATENT DOCUMENTS

| | | | |
|---|---|---|---|
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,615,065 B1 | 9/2003 | Barrett et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,745,061 B1 | 6/2004 | Hicks et al. |
| 6,748,254 B2 | 6/2004 | O'Neil et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,027,938 B1 | 4/2006 | Dister |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,120,479 B2 | 10/2006 | Chew et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |

(56)  References Cited

U.S. PATENT DOCUMENTS

| | | | |
|---|---|---|---|
| 7,519,406 | B2 | 4/2009 | Blank et al. |
| 7,526,328 | B2 | 4/2009 | Diab et al. |
| D592,507 | S | 5/2009 | Wachman et al. |
| 7,530,942 | B1 | 5/2009 | Diab |
| 7,530,949 | B2 | 5/2009 | Al Ali et al. |
| 7,530,955 | B2 | 5/2009 | Diab et al. |
| 7,563,110 | B2 | 7/2009 | Al-Ali et al. |
| 7,593,230 | B2 | 9/2009 | Abul-Haj et al. |
| 7,596,398 | B2 | 9/2009 | Al-Ali et al. |
| 7,606,608 | B2 | 10/2009 | Blank et al. |
| 7,618,375 | B2 | 11/2009 | Flaherty et al. |
| 7,620,674 | B2 | 11/2009 | Ruchti et al. |
| D606,659 | S | 12/2009 | Kiani et al. |
| 7,629,039 | B2 | 12/2009 | Eckerbom et al. |
| 7,640,140 | B2 | 12/2009 | Ruchti et al. |
| 7,647,083 | B2 | 1/2010 | Al-Ali et al. |
| D609,193 | S | 2/2010 | Al-Ali et al. |
| D614,305 | S | 4/2010 | Al-Ali et al. |
| 7,697,966 | B2 | 4/2010 | Monfre et al. |
| 7,698,105 | B2 | 4/2010 | Ruchti et al. |
| RE41,317 | E | 5/2010 | Parker |
| RE41,333 | E | 5/2010 | Blank et al. |
| 7,729,733 | B2 | 6/2010 | Al-Ali et al. |
| 7,734,320 | B2 | 6/2010 | Al-Ali |
| 7,761,127 | B2 | 7/2010 | Al-Ali et al. |
| 7,761,128 | B2 | 7/2010 | Al-Ali et al. |
| 7,764,982 | B2 | 7/2010 | Dalke et al. |
| D621,516 | S | 8/2010 | Kiani et al. |
| 7,791,155 | B2 | 9/2010 | Diab |
| 7,801,581 | B2 | 9/2010 | Diab |
| 7,822,452 | B2 | 10/2010 | Schurman et al. |
| RE41,912 | E | 11/2010 | Parker |
| 7,844,313 | B2 | 11/2010 | Kiani et al. |
| 7,844,314 | B2 | 11/2010 | Al-Ali |
| 7,844,315 | B2 | 11/2010 | Al-Ali |
| 7,873,497 | B2 | 1/2011 | Weber et al. |
| 7,880,606 | B2 | 2/2011 | Al-Ali |
| 7,880,626 | B2 | 2/2011 | Al-Ali et al. |
| 7,891,355 | B2 | 2/2011 | Al-Ali et al. |
| 7,894,868 | B2 | 2/2011 | Al-Ali et al. |
| 7,899,507 | B2 | 3/2011 | Al-Ali et al. |
| 7,904,132 | B2 | 3/2011 | Weber et al. |
| 7,909,772 | B2 | 3/2011 | Popov et al. |
| 7,910,875 | B2 | 3/2011 | Al-Ali |
| 7,919,713 | B2 | 4/2011 | Al-Ali et al. |
| 7,937,128 | B2 | 5/2011 | Al-Ali |
| 7,937,129 | B2 | 5/2011 | Mason et al. |
| 7,937,130 | B2 | 5/2011 | Diab et al. |
| 7,941,199 | B2 | 5/2011 | Kiani |
| 7,951,086 | B2 | 5/2011 | Flaherty et al. |
| 7,957,780 | B2 | 6/2011 | Lamego et al. |
| 7,962,188 | B2 | 6/2011 | Kiani et al. |
| 7,962,190 | B1 | 6/2011 | Diab et al. |
| 7,976,472 | B2 | 7/2011 | Kiani |
| 7,988,637 | B2 | 8/2011 | Diab |
| 7,990,382 | B2 | 8/2011 | Kiani |
| 7,991,446 | B2 | 8/2011 | Ali et al. |
| 8,000,761 | B2 | 8/2011 | Al-Ali |
| 8,008,088 | B2 | 8/2011 | Bellott et al. |
| RE42,753 | E | 9/2011 | Kiani-Azarbayjany et al. |
| 8,019,400 | B2 | 9/2011 | Diab et al. |
| 8,028,701 | B2 | 10/2011 | Al-Ali et al. |
| 8,029,765 | B2 | 10/2011 | Bellott et al. |
| 8,036,727 | B2 | 10/2011 | Schurman et al. |
| 8,036,728 | B2 | 10/2011 | Diab et al. |
| 8,046,040 | B2 | 10/2011 | Ali et al. |
| 8,046,041 | B2 | 10/2011 | Diab et al. |
| 8,046,042 | B2 | 10/2011 | Diab et al. |
| 8,048,040 | B2 | 11/2011 | Kiani |
| 8,050,728 | B2 | 11/2011 | Al-Ali et al. |
| RE43,169 | E | 2/2012 | Parker |
| 8,118,620 | B2 | 2/2012 | Al-Ali et al. |
| 8,126,528 | B2 | 2/2012 | Diab et al. |
| 8,128,572 | B2 | 3/2012 | Diab et al. |
| 8,130,105 | B2 | 3/2012 | Al-Ali et al. |
| 8,145,287 | B2 | 3/2012 | Diab et al. |
| 8,150,487 | B2 | 4/2012 | Diab et al. |
| 8,175,672 | B2 | 5/2012 | Parker |
| 8,180,420 | B2 | 5/2012 | Diab et al. |
| 8,182,443 | B1 | 5/2012 | Kiani |
| 8,185,180 | B2 | 5/2012 | Diab et al. |
| 8,190,223 | B2 | 5/2012 | Al-Ali et al. |
| 8,190,227 | B2 | 5/2012 | Diab et al. |
| 8,190,229 | B2 | 5/2012 | Lowery et al. |
| 8,203,438 | B2 | 6/2012 | Kiani et al. |
| 8,203,704 | B2 | 6/2012 | Merritt et al. |
| 8,204,566 | B2 | 6/2012 | Schurman et al. |
| 8,219,172 | B2 | 7/2012 | Schurman et al. |
| 8,224,411 | B2 | 7/2012 | Al-Ali et al. |
| 8,228,181 | B2 | 7/2012 | Al-Ali |
| 8,229,532 | B2 | 7/2012 | Davis |
| 8,229,533 | B2 | 7/2012 | Diab et al. |
| 8,233,955 | B2 | 7/2012 | Al-Ali et al. |
| 8,244,325 | B2 | 8/2012 | Al-Ali et al. |
| 8,255,026 | B1 | 8/2012 | Al-Ali |
| 8,255,027 | B2 | 8/2012 | Al-Ali et al. |
| 8,255,028 | B2 | 8/2012 | Al-Ali et al. |
| 8,260,577 | B2 | 9/2012 | Weber et al. |
| 8,265,723 | B1 | 9/2012 | McHale et al. |
| 8,274,360 | B2 | 9/2012 | Sampath et al. |
| 8,280,473 | B2 | 10/2012 | Al-Ali |
| 8,301,217 | B2 | 10/2012 | Al-Ali et al. |
| 8,306,596 | B2 | 11/2012 | Schurman et al. |
| 8,310,336 | B2 | 11/2012 | Muhsin et al. |
| 8,315,683 | B2 | 11/2012 | Al-Ali et al. |
| RE43,860 | E | 12/2012 | Parker |
| 8,337,403 | B2 | 12/2012 | Al-Ali et al. |
| 8,346,330 | B2 | 1/2013 | Lamego |
| 8,353,842 | B2 | 1/2013 | Al-Ali et al. |
| 8,355,766 | B2 | 1/2013 | MacNeish, III et al. |
| 8,359,080 | B2 | 1/2013 | Diab et al. |
| 8,364,223 | B2 | 1/2013 | Al-Ali et al. |
| 8,364,226 | B2 | 1/2013 | Diab et al. |
| 8,374,665 | B2 | 2/2013 | Lamego |
| 8,385,995 | B2 | 2/2013 | Al-Ali et al. |
| 8,385,996 | B2 | 2/2013 | Smith et al. |
| 8,388,353 | B2 | 3/2013 | Kiani et al. |
| 8,399,822 | B2 | 3/2013 | Al-Ali |
| 8,401,602 | B2 | 3/2013 | Kiani |
| 8,405,608 | B2 | 3/2013 | Al-Ali et al. |
| 8,414,499 | B2 | 4/2013 | Al-Ali et al. |
| 8,418,524 | B2 | 4/2013 | Al-Ali |
| 8,423,106 | B2 | 4/2013 | Lamego et al. |
| 8,428,967 | B2 | 4/2013 | Olsen et al. |
| 8,430,817 | B1 | 4/2013 | Al-Ali et al. |
| 8,437,825 | B2 | 5/2013 | Dalvi et al. |
| 8,455,290 | B2 | 6/2013 | Siskavich |
| 8,457,703 | B2 | 6/2013 | Al-Ali |
| 8,457,707 | B2 | 6/2013 | Kiani |
| 8,463,349 | B2 | 6/2013 | Diab et al. |
| 8,466,286 | B2 | 6/2013 | Bellott et al. |
| 8,471,713 | B2 | 6/2013 | Poeze et al. |
| 8,473,020 | B2 | 6/2013 | Kiani et al. |
| 8,483,787 | B2 | 7/2013 | Al-Ali et al. |
| 8,489,364 | B2 | 7/2013 | Weber et al. |
| 8,498,684 | B2 | 7/2013 | Weber et al. |
| 8,504,128 | B2 | 8/2013 | Blank et al. |
| 8,509,867 | B2 | 8/2013 | Workman et al. |
| 8,515,509 | B2 | 8/2013 | Bruinsma et al. |
| 8,523,781 | B2 | 9/2013 | Al-Ali |
| 8,529,301 | B2 | 9/2013 | Al-Ali et al. |
| 8,532,727 | B2 | 9/2013 | Ali et al. |
| 8,532,728 | B2 | 9/2013 | Diab et al. |
| D692,145 | S | 10/2013 | Al-Ali et al. |
| 8,547,209 | B2 | 10/2013 | Kiani et al. |
| 8,548,548 | B2 | 10/2013 | Al-Ali |
| 8,548,549 | B2 | 10/2013 | Schurman et al. |
| 8,548,550 | B2 | 10/2013 | Al-Ali et al. |
| 8,560,032 | B2 | 10/2013 | Al-Ali et al. |
| 8,560,034 | B1 | 10/2013 | Diab et al. |
| 8,570,167 | B2 | 10/2013 | Al-Ali |
| 8,570,503 | B2 | 10/2013 | Vo et al. |
| 8,571,617 | B2 | 10/2013 | Reichgott et al. |
| 8,571,618 | B1 | 10/2013 | Lamego et al. |

(56)                    References Cited

U.S. PATENT DOCUMENTS

| | | |
|---|---|---|
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,761,851 B2 | 6/2014 | Benni et al. |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,330 B2 | 11/2015 | Lin |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |

(56)                    References Cited

U.S. PATENT DOCUMENTS

| | | | |
|---|---|---|---|
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,636,057 B2 | 5/2017 | Scheuing et al. |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |

(56)            References Cited

U.S. PATENT DOCUMENTS

| 10,299,709 | B2 | 5/2019 | Perea et al. |
| 10,299,720 | B2 | 5/2019 | Brown et al. |
| 10,305,775 | B2 | 5/2019 | Lamego et al. |
| 10,307,111 | B2 | 6/2019 | Muhsin et al. |
| 10,325,681 | B2 | 6/2019 | Sampath et al. |
| 10,327,337 | B2 | 6/2019 | Schmidt et al. |
| 10,327,713 | B2 | 6/2019 | Barker et al. |
| 10,332,630 | B2 | 6/2019 | Al-Ali |
| 10,335,033 | B2 | 7/2019 | Al-Ali |
| 10,335,068 | B2 | 7/2019 | Poeze et al. |
| 10,335,072 | B2 | 7/2019 | Al-Ali et al. |
| 10,342,470 | B2 | 7/2019 | Al-Ali et al. |
| 10,342,487 | B2 | 7/2019 | Al-Ali et al. |
| 10,342,497 | B2 | 7/2019 | Al-Ali et al. |
| 10,349,895 | B2 | 7/2019 | Telfort et al. |
| 10,349,898 | B2 | 7/2019 | Al-Ali et al. |
| 10,354,504 | B2 | 7/2019 | Kiani et al. |
| 10,357,206 | B2 | 7/2019 | Weber et al. |
| 10,357,209 | B2 | 7/2019 | Al-Ali |
| 10,366,787 | B2 | 7/2019 | Sampath et al. |
| 10,368,787 | B2 | 8/2019 | Reichgott et al. |
| 10,376,190 | B1 | 8/2019 | Poeze et al. |
| 10,376,191 | B1 | 8/2019 | Poeze et al. |
| 10,383,520 | B2 | 8/2019 | Wojtczuk et al. |
| 10,383,527 | B2 | 8/2019 | Al-Ali |
| 10,388,120 | B2 | 8/2019 | Muhsin et al. |
| 10,398,320 | B2 | 9/2019 | Kiani et al. |
| 10,405,804 | B2 | 9/2019 | Al-Ali |
| 10,413,666 | B2 | 9/2019 | Al-Ali et al. |
| 10,420,493 | B2 | 9/2019 | Al-Ali et al. |
| D864,120 | S | 10/2019 | Forrest et al. |
| 10,433,776 | B2 | 10/2019 | Al-Ali |
| 10,441,181 | B1 | 10/2019 | Telfort et al. |
| 10,441,196 | B2 | 10/2019 | Eckerbom et al. |
| 10,448,844 | B2 | 10/2019 | Al-Ali et al. |
| 10,448,871 | B2 | 10/2019 | Al-Ali et al. |
| 10,456,038 | B2 | 10/2019 | Lamego et al. |
| 10,463,284 | B2 | 11/2019 | Al-Ali et al. |
| 10,463,340 | B2 | 11/2019 | Telfort et al. |
| 10,470,695 | B2 | 11/2019 | Al-Ali et al. |
| 10,471,159 | B1 | 11/2019 | Lapotko et al. |
| 10,478,107 | B2 | 11/2019 | Kiani et al. |
| 10,503,379 | B2 | 12/2019 | Al-Ali et al. |
| 10,505,311 | B2 | 12/2019 | Al-Ali et al. |
| 10,512,436 | B2 | 12/2019 | Muhsin et al. |
| 10,524,706 | B2 | 1/2020 | Telfort et al. |
| 10,524,738 | B2 | 1/2020 | Olsen |
| 10,531,811 | B2 | 1/2020 | Al-Ali et al. |
| 10,531,819 | B2 | 1/2020 | Diab et al. |
| 10,531,835 | B2 | 1/2020 | Al-Ali et al. |
| 10,532,174 | B2 | 1/2020 | Al-Ali |
| 10,537,285 | B2 | 1/2020 | Shreim et al. |
| 10,542,903 | B2 | 1/2020 | Al-Ali et al. |
| 10,548,561 | B2 | 2/2020 | Telfort et al. |
| 10,555,678 | B2 | 2/2020 | Dalvi et al. |
| 10,568,514 | B2 | 2/2020 | Wojtczuk et al. |
| 10,568,553 | B2 | 2/2020 | O'Neil et al. |
| RE47,882 | E | 3/2020 | Al-Ali |
| 10,608,817 | B2 | 3/2020 | Haider et al. |
| D880,477 | S | 4/2020 | Forrest et al. |
| 10,617,302 | B2 | 4/2020 | Al-Ali et al. |
| 10,617,335 | B2 | 4/2020 | Al-Ali et al. |
| 10,637,181 | B2 | 4/2020 | Al-Ali et al. |
| D886,849 | S | 6/2020 | Muhsin et al. |
| D887,548 | S | 6/2020 | Abdul-Hafiz et al. |
| D887,549 | S | 6/2020 | Abdul-Hafiz et al. |
| 10,667,764 | B2 | 6/2020 | Ahmed et al. |
| D890,708 | S | 7/2020 | Forrest et al. |
| 10,721,785 | B2 | 7/2020 | Al-Ali |
| 10,736,518 | B2 | 8/2020 | Al-Ali et al. |
| 10,750,984 | B2 | 8/2020 | Pauley et al. |
| D897,098 | S | 9/2020 | Al-Ali |
| 10,779,098 | B2 | 9/2020 | Iswanto et al. |
| 10,827,961 | B1 | 11/2020 | Iyengar et al. |
| 10,828,007 | B1 | 11/2020 | Telfort et al. |
| 10,832,818 | B2 | 11/2020 | Muhsin et al. |
| 10,849,554 | B2 | 12/2020 | Shreim et al. |
| 10,856,750 | B2 | 12/2020 | Indorf |
| D906,970 | S | 1/2021 | Forrest et al. |
| D908,213 | S | 1/2021 | Abdul-Hafiz et al. |
| 10,918,281 | B2 | 2/2021 | Al-Ali et al. |
| 10,932,705 | B2 | 3/2021 | Muhsin et al. |
| 10,932,729 | B2 | 3/2021 | Kiani et al. |
| 10,939,878 | B2 | 3/2021 | Kiani et al. |
| 10,956,950 | B2 | 3/2021 | Al-Ali et al. |
| D916,135 | S | 4/2021 | Indorf et al. |
| D917,046 | S | 4/2021 | Abdul-Hafiz et al. |
| D917,550 | S | 4/2021 | Indorf et al. |
| D917,564 | S | 4/2021 | Indorf et al. |
| D917,704 | S | 4/2021 | Al-Ali et al. |
| 10,987,066 | B2 | 4/2021 | Chandran et al. |
| 10,991,135 | B2 | 4/2021 | Al-Ali et al. |
| D919,094 | S | 5/2021 | Al-Ali et al. |
| D919,100 | S | 5/2021 | Al-Ali et al. |
| 11,006,867 | B2 | 5/2021 | Al-Ali |
| D921,202 | S | 6/2021 | Al-Ali et al. |
| 11,024,064 | B2 | 6/2021 | Muhsin et al. |
| 11,026,604 | B2 | 6/2021 | Chen et al. |
| D925,597 | S | 7/2021 | Chandran et al. |
| D927,699 | S | 8/2021 | Al-Ali et al. |
| 11,076,777 | B2 | 8/2021 | Lee et al. |
| 11,114,188 | B2 | 9/2021 | Poeze et al. |
| D933,232 | S | 10/2021 | Al-Ali et al. |
| D933,233 | S | 10/2021 | Al-Ali et al. |
| D933,234 | S | 10/2021 | Al-Ali et al. |
| 11,145,408 | B2 | 10/2021 | Sampath et al. |
| 11,147,518 | B1 | 10/2021 | Al-Ali et al. |
| 11,185,262 | B2 | 11/2021 | Al-Ali et al. |
| 11,191,484 | B2 | 12/2021 | Kiani et al. |
| D946,596 | S | 3/2022 | Ahmed |
| D946,597 | S | 3/2022 | Ahmed |
| D946,598 | S | 3/2022 | Ahmed |
| D946,617 | S | 3/2022 | Ahmed |
| 11,272,839 | B2 | 3/2022 | Al-Ali et al. |
| 11,289,199 | B2 | 3/2022 | Al-Ali |
| RE49,034 | E | 4/2022 | Al-Ali |
| 11,298,021 | B2 | 4/2022 | Muhsin et al. |
| D950,580 | S | 5/2022 | Ahmed |
| D950,599 | S | 5/2022 | Ahmed |
| D950,738 | S | 5/2022 | Al-Ali et al. |
| D957,648 | S | 7/2022 | Al-Ali |
| 11,382,567 | B2 | 7/2022 | O'Brien et al. |
| 11,389,093 | B2 | 7/2022 | Triman et al. |
| 11,406,286 | B2 | 8/2022 | Al-Ali et al. |
| 11,417,426 | B2 | 8/2022 | Muhsin et al. |
| 11,439,329 | B2 | 9/2022 | Lamego |
| 11,445,948 | B2 | 9/2022 | Scruggs et al. |
| D965,789 | S | 10/2022 | Al-Ali et al. |
| D967,433 | S | 10/2022 | Al-Ali et al. |
| 11,464,410 | B2 | 10/2022 | Muhsin |
| 11,504,058 | B1 | 11/2022 | Sharma et al. |
| 11,504,066 | B1 | 11/2022 | Dalvi et al. |
| D971,933 | S | 12/2022 | Ahmed |
| D973,072 | S | 12/2022 | Ahmed |
| D973,685 | S | 12/2022 | Ahmed |
| D973,686 | S | 12/2022 | Ahmed |
| D974,193 | S | 1/2023 | Forrest et al. |
| D979,516 | S | 2/2023 | Al-Ali et al. |
| D980,091 | S | 3/2023 | Forrest et al. |
| 11,596,363 | B2 | 3/2023 | Lamego |
| 11,627,919 | B2 | 4/2023 | Kiani et al. |
| 11,637,437 | B2 | 4/2023 | Al-Ali et al. |
| D985,498 | S | 5/2023 | Al-Ali et al. |
| 11,653,862 | B2 | 5/2023 | Dalvi et al. |
| D989,112 | S | 6/2023 | Muhsin et al. |
| D989,327 | S | 6/2023 | Al-Ali et al. |
| 11,678,829 | B2 | 6/2023 | Al-Ali et al. |
| 11,679,579 | B2 | 6/2023 | Al-Ali |
| 11,684,296 | B2 | 6/2023 | Vo et al. |
| 11,692,934 | B2 | 7/2023 | Normand et al. |
| 11,701,043 | B2 | 7/2023 | Al-Ali et al. |
| D997,365 | S | 8/2023 | Hwang |
| 11,721,105 | B2 | 8/2023 | Ranasinghe et al. |
| 11,730,379 | B2 | 8/2023 | Ahmed et al. |

(56)                    References Cited

U.S. PATENT DOCUMENTS

| | | | |
|---|---|---|---|
| D998,625 S | 9/2023 | Indorf et al. | |
| D998,630 S | 9/2023 | Indorf et al. | |
| D998,631 S | 9/2023 | Indorf et al. | |
| D999,244 S | 9/2023 | Indorf et al. | |
| D999,245 S | 9/2023 | Indorf et al. | |
| D999,246 S | 9/2023 | Indorf et al. | |
| 11,751,780 B2 | 9/2023 | Al-Ali et al. | |
| 11,766,198 B2 | 9/2023 | Pauley et al. | |
| D1,000,975 S | 10/2023 | Al-Ali et al. | |
| 11,803,623 B2 | 10/2023 | Kiani et al. | |
| 11,832,940 B2 | 12/2023 | Diab et al. | |
| D1,013,179 S | 1/2024 | Al-Ali et al. | |
| 11,872,156 B2 | 1/2024 | Telfort et al. | |
| 11,879,960 B2 | 1/2024 | Ranasinghe et al. | |
| 11,883,129 B2 | 1/2024 | Olsen | |
| D1,022,729 S | 4/2024 | Forrest et al. | |
| 11,951,186 B2 | 4/2024 | Krishnamani et al. | |
| 11,974,833 B2 | 5/2024 | Forrest et al. | |
| 11,986,067 B2 | 5/2024 | Al-Ali et al. | |
| 11,986,289 B2 | 5/2024 | Dalvi et al. | |
| 11,986,305 B2 | 5/2024 | Al-Ali et al. | |
| D1,031,729 S | 6/2024 | Forrest et al. | |
| 12,004,869 B2 | 6/2024 | Kiani et al. | |
| 12,014,328 B2 | 6/2024 | Wachman et al. | |
| D1,036,293 S | 7/2024 | Al-Ali et al. | |
| D1,037,462 S | 7/2024 | Al-Ali et al. | |
| 12,029,844 B2 | 7/2024 | Pauley et al. | |
| 12,048,534 B2 | 7/2024 | Vo et al. | |
| 12,064,217 B2 | 8/2024 | Ahmed et al. | |
| 12,066,426 B1 | 8/2024 | Lapotko et al. | |
| D1,041,511 S | 9/2024 | Indorf et al. | |
| D1,042,596 S | 9/2024 | DeJong et al. | |
| D1,042,852 S | 9/2024 | Hwang | |
| 12,076,159 B2 | 9/2024 | Belur Nagaraj et al. | |
| 12,082,926 B2 | 9/2024 | Sharma et al. | |
| D1,044,828 S | 10/2024 | Chandran et al. | |
| D1,048,571 S | 10/2024 | Yu et al. | |
| D1,048,908 S | 10/2024 | Al-Ali et al. | |
| 12,106,752 B2 | 10/2024 | Campbell et al. | |
| 12,114,974 B2 | 10/2024 | Al-Ali et al. | |
| 12,126,683 B2 | 10/2024 | Koo et al. | |
| 12,127,838 B2 | 10/2024 | Olsen et al. | |
| 12,128,213 B2 | 10/2024 | Kiani et al. | |
| 12,131,661 B2 | 10/2024 | Pauley et al. | |
| D1,050,910 S | 11/2024 | Al-Ali et al. | |
| 12,178,572 B1 | 12/2024 | Pauley et al. | |
| 12,178,581 B2 | 12/2024 | Telfort et al. | |
| 12,178,852 B2 | 12/2024 | Kiani et al. | |
| D1,057,159 S | 1/2025 | DeJong et al. | |
| D1,057,160 S | 1/2025 | DeJong et al. | |
| 12,198,790 B1 | 1/2025 | Al-Ali | |
| 12,200,421 B2 | 1/2025 | Campbell et al. | |
| 12,207,901 B1 | 1/2025 | Lapotko et al. | |
| D1,060,680 S | 2/2025 | Al-Ali et al. | |
| D1,061,585 S | 2/2025 | Indorf | |
| D1,063,893 S | 2/2025 | DeJong et al. | |
| 12,220,207 B2 | 2/2025 | Telfort et al. | |
| 12,235,941 B2 | 2/2025 | Kiani et al. | |
| 12,236,767 B2 | 2/2025 | Muhsin | |
| D1,066,244 S | 3/2025 | Lim et al. | |
| D1,066,672 S | 3/2025 | Al-Ali et al. | |
| D1,068,656 S | 4/2025 | Trevisan et al. | |
| D1,071,195 S | 4/2025 | Seung | |
| D1,072,836 S | 4/2025 | Indorf | |
| D1,072,837 S | 4/2025 | Ahmed et al. | |
| 12,272,445 B1 | 4/2025 | Kiani | |
| D1,078,689 S | 6/2025 | Hwang | |
| D1,079,020 S | 6/2025 | Hwang | |
| 12,336,796 B2 | 6/2025 | Al-Ali | |
| 2001/0034477 A1 | 10/2001 | Mansfield et al. | |
| 2001/0039483 A1 | 11/2001 | Brand et al. | |
| 2002/0010401 A1 | 1/2002 | Bushmakin et al. | |
| 2002/0058864 A1 | 5/2002 | Mansfield et al. | |
| 2002/0133080 A1 | 9/2002 | Apruzzese et al. | |
| 2003/0013975 A1 | 1/2003 | Kiani | |
| 2003/0018243 A1 | 1/2003 | Gerhardt et al. | |
| 2003/0109775 A1 | 6/2003 | O'Neil et al. | |
| 2003/0144582 A1 | 7/2003 | Cohen et al. | |
| 2003/0156288 A1 | 8/2003 | Barnum et al. | |
| 2003/0212312 A1 | 11/2003 | Coffin et al. | |
| 2003/0225323 A1 | 12/2003 | Kiani et al. | |
| 2004/0106163 A1 | 6/2004 | Workman et al. | |
| 2005/0055276 A1 | 3/2005 | Kiani et al. | |
| 2005/0234317 A1 | 10/2005 | Kiani | |
| 2006/0073719 A1 | 4/2006 | Kiani | |
| 2006/0161054 A1 | 7/2006 | Reuss et al. | |
| 2006/0189871 A1 | 8/2006 | Al-Ali et al. | |
| 2006/0217608 A1 | 9/2006 | Fain | |
| 2007/0073116 A1 | 3/2007 | Kiani et al. | |
| 2007/0149864 A1 | 6/2007 | Laakkonen | |
| 2007/0180140 A1 | 8/2007 | Welch et al. | |
| 2007/0244377 A1 | 10/2007 | Cozad et al. | |
| 2007/0282478 A1 | 12/2007 | Al-Ali et al. | |
| 2008/0064965 A1 | 3/2008 | Jay et al. | |
| 2008/0094228 A1 | 4/2008 | Welch et al. | |
| 2008/0103375 A1 | 5/2008 | Kiani | |
| 2008/0221418 A1 | 9/2008 | Al-Ali et al. | |
| 2009/0036759 A1 | 2/2009 | Ault et al. | |
| 2009/0093687 A1 | 4/2009 | Telfort et al. | |
| 2009/0095926 A1 | 4/2009 | MacNeish, III | |
| 2009/0131770 A1 | 5/2009 | Scheuing et al. | |
| 2009/0163775 A1 | 6/2009 | Barrett | |
| 2009/0182209 A1 | 7/2009 | Benni | |
| 2009/0247924 A1 | 10/2009 | Harima et al. | |
| 2009/0247984 A1 | 10/2009 | Lamego et al. | |
| 2009/0275813 A1 | 11/2009 | Davis | |
| 2009/0275844 A1 | 11/2009 | Al-Ali | |
| 2009/0299157 A1 | 12/2009 | Telfort et al. | |
| 2010/0004518 A1 | 1/2010 | Vo et al. | |
| 2010/0030040 A1 | 2/2010 | Poeze et al. | |
| 2010/0049018 A1 | 2/2010 | Duffy et al. | |
| 2010/0069725 A1 | 3/2010 | Al-Ali | |
| 2010/0099964 A1 | 4/2010 | O'Reilly et al. | |
| 2010/0234718 A1 | 9/2010 | Sampath et al. | |
| 2010/0261979 A1 | 10/2010 | Al-Ali et al. | |
| 2010/0270257 A1 | 10/2010 | Wachman et al. | |
| 2010/0317936 A1 | 12/2010 | Al-Ali et al. | |
| 2011/0001605 A1 | 1/2011 | Kiani et al. | |
| 2011/0028806 A1 | 2/2011 | Merritt et al. | |
| 2011/0028809 A1 | 2/2011 | Goodman | |
| 2011/0040197 A1 | 2/2011 | Welch et al. | |
| 2011/0077473 A1 | 3/2011 | Lisogurski | |
| 2011/0082711 A1 | 4/2011 | Poeze et al. | |
| 2011/0087081 A1 | 4/2011 | Kiani et al. | |
| 2011/0112379 A1 | 5/2011 | Li et al. | |
| 2011/0118561 A1 | 5/2011 | Tari et al. | |
| 2011/0125060 A1 | 5/2011 | Telfort et al. | |
| 2011/0137297 A1 | 6/2011 | Kiani et al. | |
| 2011/0172498 A1 | 7/2011 | Olsen et al. | |
| 2011/0172967 A1 | 7/2011 | Al-Ali et al. | |
| 2011/0190600 A1 | 8/2011 | McKenna et al. | |
| 2011/0208015 A1 | 8/2011 | Welch et al. | |
| 2011/0209915 A1 | 9/2011 | Telfort et al. | |
| 2011/0213212 A1 | 9/2011 | Al-Ali | |
| 2011/0213274 A1 | 9/2011 | Telfort et al. | |
| 2011/0230733 A1 | 9/2011 | Al-Ali | |
| 2011/0237911 A1 | 9/2011 | Lamego et al. | |
| 2011/0237969 A1 | 9/2011 | Eckerbom et al. | |
| 2012/0041316 A1 | 2/2012 | Al Ali et al. | |
| 2012/0059267 A1 | 3/2012 | Lamego et al. | |
| 2012/0116175 A1 | 5/2012 | Al-Ali et al. | |
| 2012/0123231 A1 | 5/2012 | O'Reilly | |
| 2012/0165629 A1 | 6/2012 | Merritt et al. | |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0226117 A1 | 9/2012 | Lamego et al. | |
| 2012/0227739 A1 | 9/2012 | Kiani | |
| 2012/0253163 A1 | 10/2012 | Afanasewicz et al. | |
| 2012/0265039 A1 | 10/2012 | Kiani | |
| 2012/0283524 A1 | 11/2012 | Kiani et al. | |
| 2012/0286955 A1 | 11/2012 | Welch et al. | |
| 2012/0296178 A1 | 11/2012 | Lamego et al. | |
| 2012/0302894 A1 | 11/2012 | Diab et al. | |

(56)     References Cited

U.S. PATENT DOCUMENTS

| | | |
|---|---|---|
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0079610 A1 | 3/2013 | Al-Ali |
| 2013/0079618 A1 | 3/2013 | Sandmore et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0109938 A1 | 5/2013 | Kuhn |
| 2013/0162433 A1 | 6/2013 | Muhsin et al. |
| 2013/0178725 A1 | 7/2013 | O'Neil et al. |
| 2013/0178749 A1 | 7/2013 | Lamego |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0237782 A1 | 9/2013 | Lisogurski |
| 2013/0243021 A1 | 9/2013 | Siskavich |
| 2013/0244453 A1 | 9/2013 | Sakamoto |
| 2013/0253334 A1 | 9/2013 | Al-Ali et al. |
| 2013/0262730 A1 | 10/2013 | Al-Ali et al. |
| 2013/0274571 A1 | 10/2013 | Diab et al. |
| 2013/0278802 A1 | 10/2013 | Attar et al. |
| 2013/0296672 A1 | 11/2013 | O'Neil et al. |
| 2013/0296713 A1 | 11/2013 | Al-Ali et al. |
| 2013/0317327 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0324817 A1 | 12/2013 | Diab |
| 2013/0324855 A1 | 12/2013 | Lisogurski et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2013/0345921 A1 | 12/2013 | Al-Ali et al. |
| 2014/0012100 A1 | 1/2014 | Al-Ali et al. |
| 2014/0022256 A1 | 1/2014 | Carnes et al. |
| 2014/0025306 A1 | 1/2014 | Weber et al. |
| 2014/0031650 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0058233 A1 | 2/2014 | Koyama et al. |
| 2014/0066783 A1 | 3/2014 | Kiani et al. |
| 2014/0073167 A1 | 3/2014 | Al-Ali et al. |
| 2014/0077956 A1 | 3/2014 | Sampath et al. |
| 2014/0081097 A1 | 3/2014 | Al-Ali et al. |
| 2014/0081100 A1 | 3/2014 | Muhsin et al. |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0142399 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0155712 A1 | 6/2014 | Lamego et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275875 A1 | 9/2014 | Su et al. |
| 2014/0275881 A1 | 9/2014 | Lamego et al. |
| 2014/0275932 A1 | 9/2014 | Zadig |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0051464 A1 | 2/2015 | Ozaki et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0133755 A1 | 5/2015 | Smith et al. |
| 2015/0165312 A1 | 6/2015 | Kiani |
| 2015/0196237 A1 | 7/2015 | Lamego |
| 2015/0196249 A1 | 7/2015 | Brown et al. |
| 2015/0208966 A1 | 7/2015 | Al-Ali |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366507 A1 | 12/2015 | Blank |
| 2016/0007930 A1 | 1/2016 | Weber et al. |
| 2016/0029932 A1 | 2/2016 | Al-Ali |
| 2016/0051205 A1 | 2/2016 | Al-Ali et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |

(56) References Cited

U.S. PATENT DOCUMENTS

| | | |
|---|---|---|
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0021099 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224216 A1 | 8/2017 | Al-Ali |
| 2017/0224231 A1 | 8/2017 | Al-Ali |
| 2017/0224233 A1 | 8/2017 | Al-Ali |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |

(56) References Cited

U.S. PATENT DOCUMENTS

| | | |
|---|---|---|
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0307377 A1 | 10/2019 | Perea et al. |
| 2019/0320906 A1 | 10/2019 | Olsen |
| 2019/0320959 A1 | 10/2019 | Al-Ali |
| 2019/0320988 A1 | 10/2019 | Ahmed et al. |
| 2019/0325722 A1 | 10/2019 | Kiani et al. |
| 2019/0350506 A1 | 11/2019 | Al-Ali et al. |
| 2019/0357813 A1 | 11/2019 | Poeze et al. |
| 2019/0357823 A1 | 11/2019 | Reichgott et al. |
| 2019/0357824 A1 | 11/2019 | Al-Ali et al. |
| 2019/0358524 A1 | 11/2019 | Kiani |
| 2019/0365294 A1 | 12/2019 | Poeze et al. |
| 2019/0374135 A1 | 12/2019 | Poeze et al. |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2019/0386908 A1 | 12/2019 | Lamego et al. |
| 2019/0388039 A1 | 12/2019 | Al-Ali |
| 2020/0000338 A1 | 1/2020 | Lamego et al. |
| 2020/0000340 A1 | 1/2020 | Wojtczuk et al. |
| 2020/0000415 A1 | 1/2020 | Barker et al. |
| 2020/0015716 A1 | 1/2020 | Poeze et al. |
| 2020/0021930 A1 | 1/2020 | Iswanto et al. |
| 2020/0029867 A1 | 1/2020 | Poeze et al. |
| 2020/0037453 A1 | 1/2020 | Triman et al. |
| 2020/0037891 A1 | 2/2020 | Kiani et al. |
| 2020/0037966 A1 | 2/2020 | Al-Ali |
| 2020/0046257 A1 | 2/2020 | Eckerbom et al. |
| 2020/0054253 A1 | 2/2020 | Al-Ali et al. |
| 2020/0060591 A1 | 2/2020 | Diab et al. |
| 2020/0060628 A1 | 2/2020 | Al-Ali et al. |
| 2020/0060629 A1 | 2/2020 | Muhsin et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkvist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2024/0404549 A1 | 12/2024 | Campbell et al. |
| 2025/0000458 A1 | 1/2025 | Abdul-Hafiz et al. |
| 2025/0037836 A1 | 1/2025 | Kiani |

(56) References Cited

U.S. PATENT DOCUMENTS

| | | |
|---|---|---|
| 2025/0100482 A1 | 3/2025 | Al-Ali et al. |
| 2025/0118415 A1 | 4/2025 | Olsen |

FOREIGN PATENT DOCUMENTS

| | | |
|---|---|---|
| JP | H06-505904 | 7/1994 |
| JP | H09-501074 | 2/1997 |
| JP | 2009-509663 | 3/2009 |
| JP | 2010-155159 | 7/2010 |
| JP | 2011-519591 | 7/2011 |
| WO | WO 98/016152 | 4/1998 |
| WO | WO 00/059374 | 10/2000 |
| WO | WO 03/031961 | 4/2003 |
| WO | WO 2012/109661 | 8/2012 |
| WO | WO 2015/054161 | 4/2015 |
| WO | WO 2015/054166 | 4/2015 |

OTHER PUBLICATIONS

US 2024/0016391 A1, 01/2024, Lapotko et al. (withdrawn)

International Search Report and Written Opinion in International Application No. PCT/US2014/059374, mailed on Jan. 8, 2015.

International Search Report and Written Opinion in International Application No. PCT/US2014/059366, mailed on Apr. 20, 2015.

Office Action received in Japanese Application No. 2016-520617 dated Sep. 3, 2018, in 3 pages.

Office Action received in Japanese Application No. 2019-025513 dated Feb. 3, 2020, in 4 pages.

Office Action received in Japanese Application No. 2019-025513 dated Jun. 15, 2020, in 4 pages.

Letter from Shawn W. Forrest to Masimo Corporation re 510(k) No. K160526, U.S. Food & Drug Administration, dated Jun. 9, 2016 in 11 pages.

Letter from William J. Heetderks to Masimo Corporation re 510(k) No. K162603, U.S. Food & Drug Administration, dated May 26, 2017 in 11 pages.

Letter from Jay R. Gupta to Masimo Corporation re 510(k) No. K182429, U.S. Food & Drug Administration, dated Jun. 7, 2019 in 9 pages.

Letter from Colin K. Chen to Masimo Corporation re 510(k) No. K201432, U.S. Food & Drug Administration, dated Aug. 29, 2020 in 10 pages.

Letter from Jianting Wang to Masimo Corporation re 510(k) No. K214072, U.S. Food & Drug Administration, dated Mar. 31, 2022 in 12 pages.

* cited by examiner

SECTION A-A

SECTION B-B

SECTION A-A

SECTION B-B

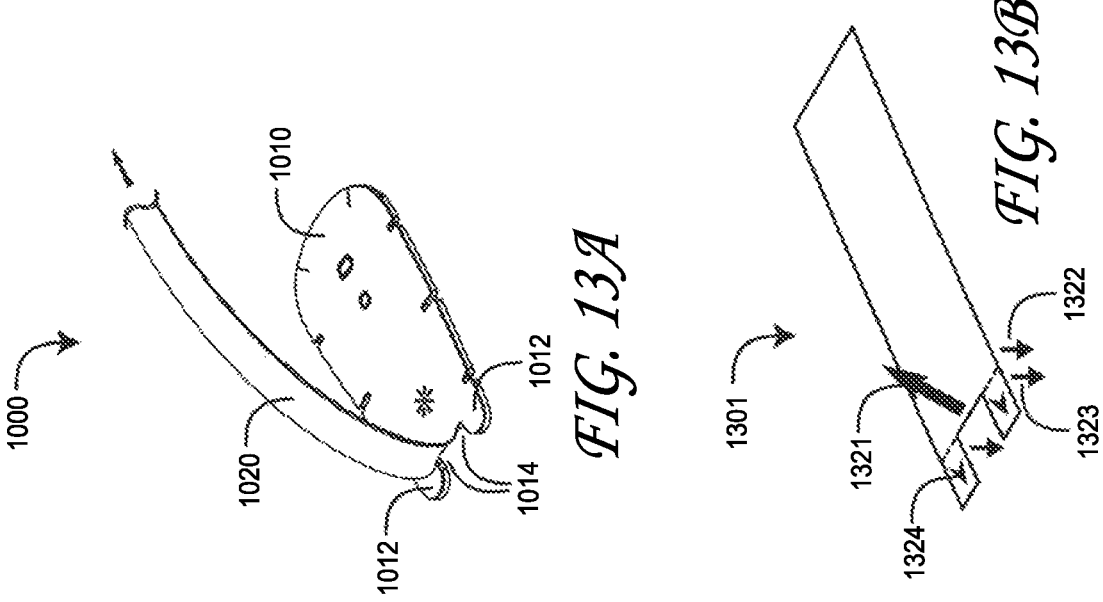
FIG. 13A
FIG. 13B
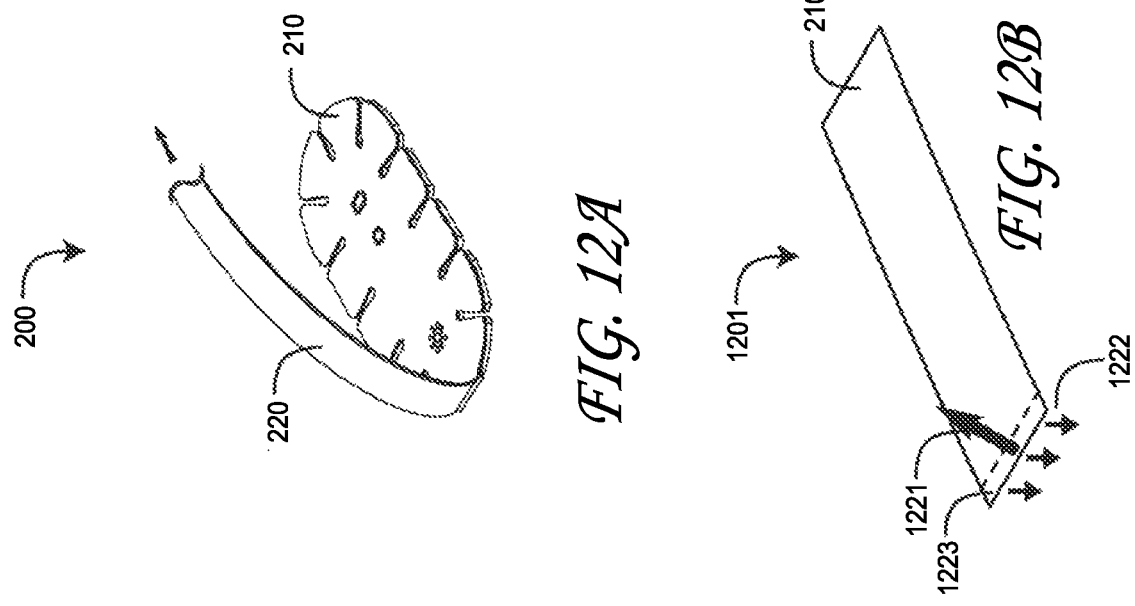
FIG. 12A
FIG. 12B

REGIONAL OXIMETRY SENSOR

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present application is a continuation of U.S. patent application Ser. No. 16/745,894, filed Jan. 17, 2020, titled Regional Oximetry Sensor, which is itself a continuation of U.S. patent application Ser. No. 15/891,910, filed Feb. 8, 2018, titled Regional Oximetry Sensor, now issued as U.S. Pat. No. 10,617,335, which is a continuation of U.S. patent application Ser. No. 14/507,620, filed Oct. 6, 2014, titled Regional Oximetry Sensor, which claims priority benefit under 35 U.S.C. § 119(e) to U.S. Provisional Patent Application Ser. No. 62/012,170, filed Jun. 13, 2014, titled Peel-Off Resistant Regional Oximetry Sensor; U.S. Provisional Patent Application Ser. No. 61/887,878 filed Oct. 7, 2013, titled Regional Oximetry Pod; U.S. Provisional Patent Application Ser. No. 61/887,856 filed Oct. 7, 2013, titled Regional Oximetry Sensor; and U.S. Provisional Patent Application Ser. No. 61/887,883 filed Oct. 7, 2013, titled Regional Oximetry User Interface; all of the above-referenced provisional patent applications are hereby incorporated in their entireties by reference herein.

FIELD

The present disclosure relates to the field of optical based physiological sensors.

BACKGROUND

Regional oximetry, also referred to as tissue oximetry and cerebral oximetry, enables the continuous assessment of the oxygenation of tissue. The measurement is taken by placing one or more sensors on a patient, frequently on the patient's left and right forehead. Regional oximetry estimates regional tissue oxygenation by transcutaneous measurement of areas that are vulnerable to changes in oxygen supply and demand. Regional oximetry exploits the ability of light to penetrate tissue and determine hemoglobin oxygenation according to the amount of light absorbed by hemoglobin.

Regional oximetry differs from pulse oximetry in that tissue sampling represents primarily (70-75%) venous, and less (20-25%) arterial blood. The technique uses two photo-detectors with each light source, thereby allowing selective sampling of tissue beyond a specified depth beneath the skin. Near-field photo-detection is subtracted from far-field photo-detection to provide selective tissue oxygenation measurement beyond a pre-defined depth. Moreover, regional oximetry monitoring does not depend upon pulsa-tile flow.

Regional oximetry is a useful patient monitoring tech-nique to alert clinicians to dangerous clinical conditions. Changes in regional oximetry have been shown to occur in the absence of changes in arterial saturation or systemic hemodynamic parameters.

SUMMARY

The present disclosure provides a regional oximetry sen-sor. The regional oximetry sensor includes, for example, a face tape layer and a base tape layer adhesively attachable to a patient skin surface. The regional oximetry sensor also includes at least one emitter configured to transmit optical radiation into the patient skin surface, a near-field detector configured to detect the optical radiation after attenuation by tissue of the patient and a far field detector also configured to detect the optical radiation after attenuation by tissue of the patient. In an embodiment, the regional oximetry sensor also includes one or more focus elements associated with one or more of the emitter, the near-field detector and the far field detector. In an embodiment any or all of the emitter, near-field detector and far field detector can be provided with a focus element. The focus element improves optical transmissions by gently pushing into the skin and providing improved optical coupling with the skin.

The focus element can include a half-dome shape or any three dimensional shape that gently pushes into the skin to improve optical coupling. The focus element can also have a rectangular planar base in order to provide a support structure for cooperating with the face tape layer and/or other portions of the regional oximetry sensor. In an embodi-ment, the focus element associated with the near-field detec-tor is smaller than the focus element associated with the far field detector. For example, the near field detector includes a square shape whereas the far field detector includes a larger rectangular shape.

In an embodiment of the regional oximetry sensor, the regional oximetry sensor can have a face tape layer and a base tape layer adhesively attachable to a patient skin surface as discussed above. The sensor can also have at least one emitter configured to transmit optical radiation into the patient skin surface, a near-field detector configured to detect the optical radiation after attenuation by tissue of the patient, and a far field detector also configured to detect the optical radiation after attenuation by tissue of the patient. In some embodiments, the face tape layer and the base tape layer include a plurality of notches forming a plurality of cutouts. The plurality of cutouts can be formed in a portion of a periphery or across the entire periphery of the base and face tape layers, for example. The cutouts are mechanically decoupled from each other. Due to the mechanical decou-pling, the cutouts allow for greater ease of patient movement of the measurement site. This reduces patient discomfort while wearing the regional sensor.

In an embodiment, a peel-off resistant regional oximetry sensor is disclosed. The peel-off resistant regional oximetry sensor includes a head attachable to a patient skin surface and configured to transmit optical radiation into the skin and receive that optical radiation after attenuation by blood flow within the skin and a stem extending from the sensor head and configured to transmit electrical signals between the sensor head and an attached cable. The stem is terminated interior to the sensor head and away from an edge of the sensor head so as to define feet along either side of the stem distal the stem termination.

BRIEF DESCRIPTION OF THE DRAWINGS

The drawings and following associated descriptions are provided to illustrate embodiments of the present disclosure and do not limit the scope of the claims. Corresponding numerals indicate corresponding parts, and the leading digit of each numbered item indicates the first figure in which an item is found.

FIGS. 12A, 12B, 13A and 13B are side-by-side, top perspective views of a regional oximetry sensor and a peel-off resistant regional oximetry sensor subjected to like pulling forces and the corresponding impact of anti-peel feet extending from the cable-side of the peel-off resistant regional oximetry sensor.

DETAILED DESCRIPTION

Aspects of the disclosure will now be set forth in detail with respect to the figures and various embodiments. One of skill in the art will appreciate, however, that other embodiments and configurations of the devices and methods disclosed herein will still fall within the scope of this disclosure even if not described in the same detail as some other embodiments. Aspects of various embodiments discussed do not limit the scope of the disclosure herein, which is instead defined by the claims following this description.

Figure 1:
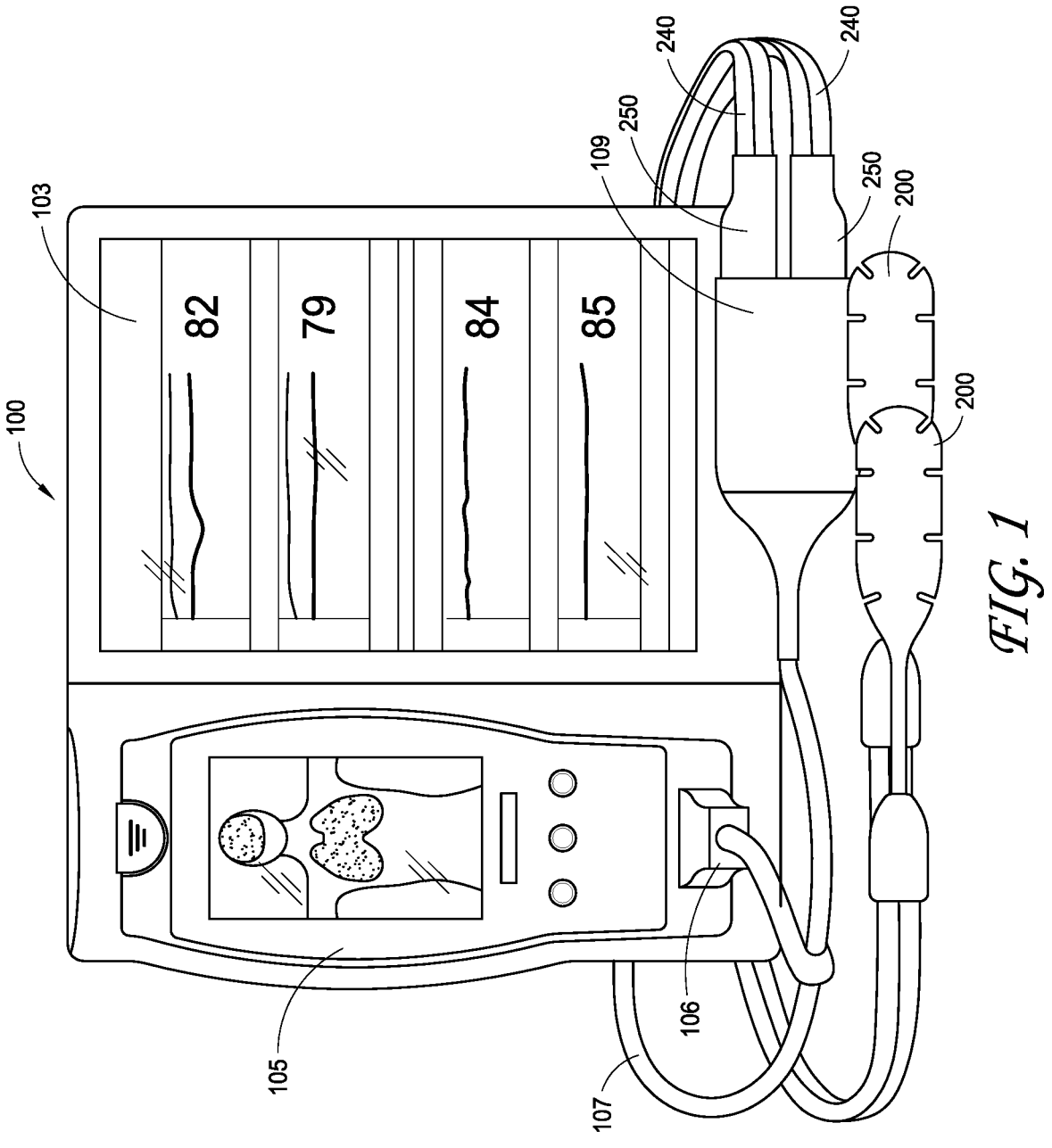
FIG. 1 is a depiction of a patient monitoring system including regional oximetry sensors and a processing and display unit.

FIG. 1 is a physiological monitoring system 100 configured to measure and display regional oximetry measurements. The physiological monitoring system 100 includes at least a display 103 and a processor (not shown) for processing and displaying physiological measurements. The physiological monitoring system 100 also includes at least one sensor 200 for detecting physiological information and providing that physiological information to the processor of the physiological monitoring system 100. In the embodiment of FIG. 1, the physiological monitoring system includes a removable hand held physiological monitor 105. The physiological monitoring system 100 of FIG. 1 also includes a sensor cable system 106 that includes wiring 107 and a sensor connector 109. Sensor connector 109 includes ports for two or more sensors. The sensors are described in more detail with respect to FIGS. 2A-2C.

Figures 2A, 2B, 2C:
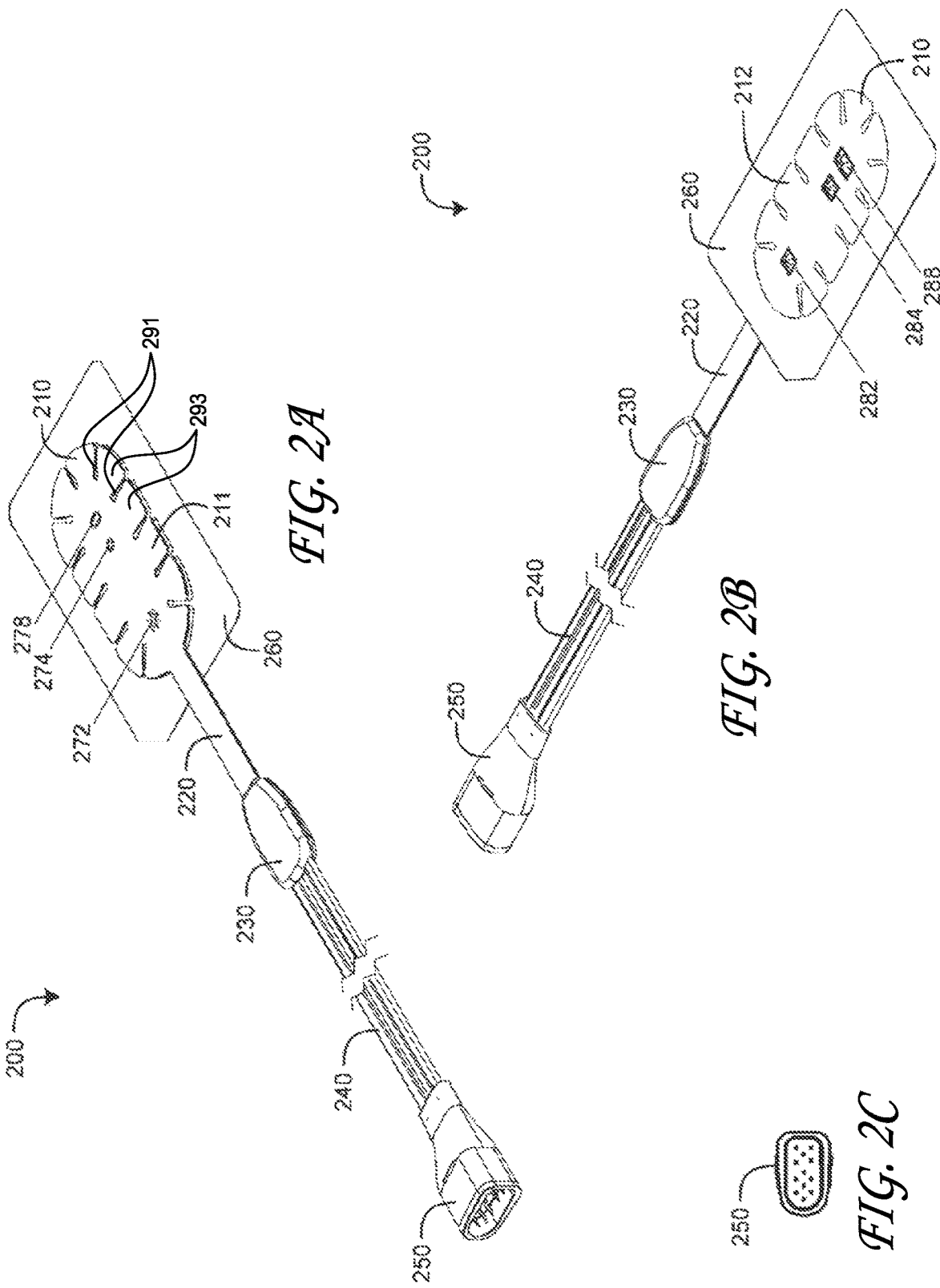
FIGS. 2A-C are top and bottom perspective views and a connector-end view, respectively, of a regional oximetry sensor.

FIGS. 2A-C illustrate a regional oximetry sensor 200 embodiment having a sensor head 210, stem 220, shell 230, cable 240 and connector 250. The sensor head 210 houses an emitter 282, a near-field detector 284 and a far-field detector 288 within a layered tape having a top side 211 and an adhesive bottom side 212 disposed on a release liner 260. The release liner 260 is removed so as to adhere the bottom side 212 to a skin surface. The sensor head 210 also includes notches or channels 291 that form cutouts 293. The cutouts 293 are independently flexible from other neighboring cutouts. Because of the various placement locations of the sensors on the human body and the movement forces placed on regional oximetry sensors, the cutouts 293 allow the sensor head 210 to be relatively large to increase the measurement area and adhesive surface area without greatly inhibiting patient movement. Thus, for example, when a patient moves their forehead with a sensor 200 adhesively attached, the sensor allows for some movement of the underlying skin so that the patient is more comfortable, yet provide a large enough surface area to provide good measurement and adhesive qualities.

The regional oximetry sensor 200 is substantially flat, allowing the sensor to adhere to the patient without significant bulges. The stem 220 extends out radially outward from the sensor head 210. The stem is positioned to extend from a radial edge in order to provide a clean exit from the body for wiring and cables. The radial placement also provides for streamlined sensor construction and prevents unnecessary bending or wrapping of internal or external wires.

The emitter 282 and detectors 284, 288 have a lens that protrudes from the bottom side 212, advantageously providing a robust optics-skin interface. The top side 211 has emitter/detector indicators 272-278 so as to aid precise sensor placement on a patient site. The shell 230 houses the stem 220 to cable 240 interconnect, described in detail with respect to FIGS. 3A-C, below. The connector 250 is a 12-pin, D-shaped plug.

Figures 3A, 3B, 3C:
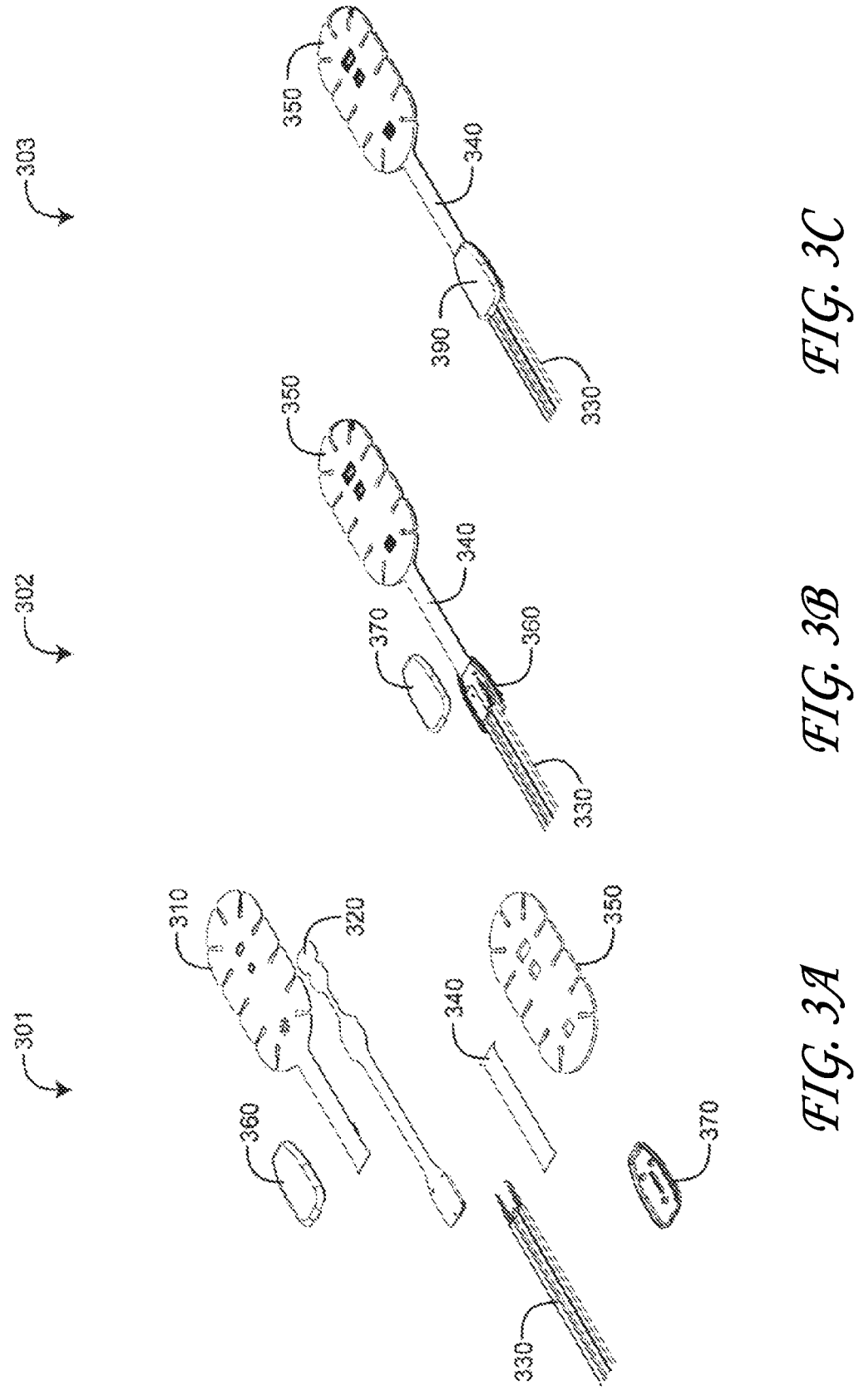
FIGS. 3A-C are top exploded, bottom partially-exploded and bottom assembled perspective views, respectively, of regional oximetry sensor head, stem and shell assemblies.

FIGS. 3A-C illustrate an assembly of a regional oximetry sensor portion including a head assembly (FIG. 3A) and a sensor cable to flex circuit interconnect (FIGS. 3B-C). As shown in FIG. 3A, a sensor head assembly 301 has a face tape 310, a flex circuit 320, a sensor cable 330, a stem tape 340, a base tape 350, a shell top 360 and a shell base 370. The face tape 310 and base tape 350 encase the flex circuit 320 and corresponding emitter and detectors. The shell top and base 360, 370 encase the sensor cable 330 to flex circuit 320 interconnect, described in further detail with respect to FIGS. 4A-B, below. The stem tape 340 encases the flex circuit 320 below the base tape 350.

Figure 4:
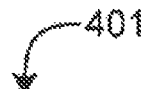
FIG. 4 is a bottom plan view a sensor cable and sensor flex circuit interconnection.
Figure 4:
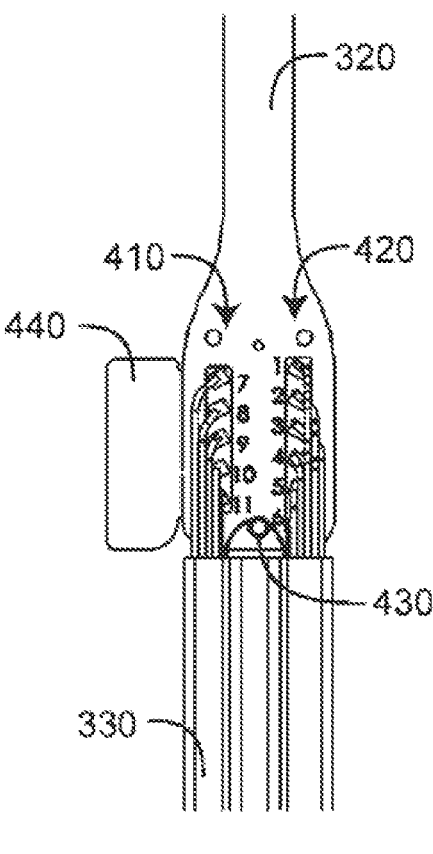
Figures 5A, 5B, 5C, 5D, 5E, 5F, 5G, 5H:
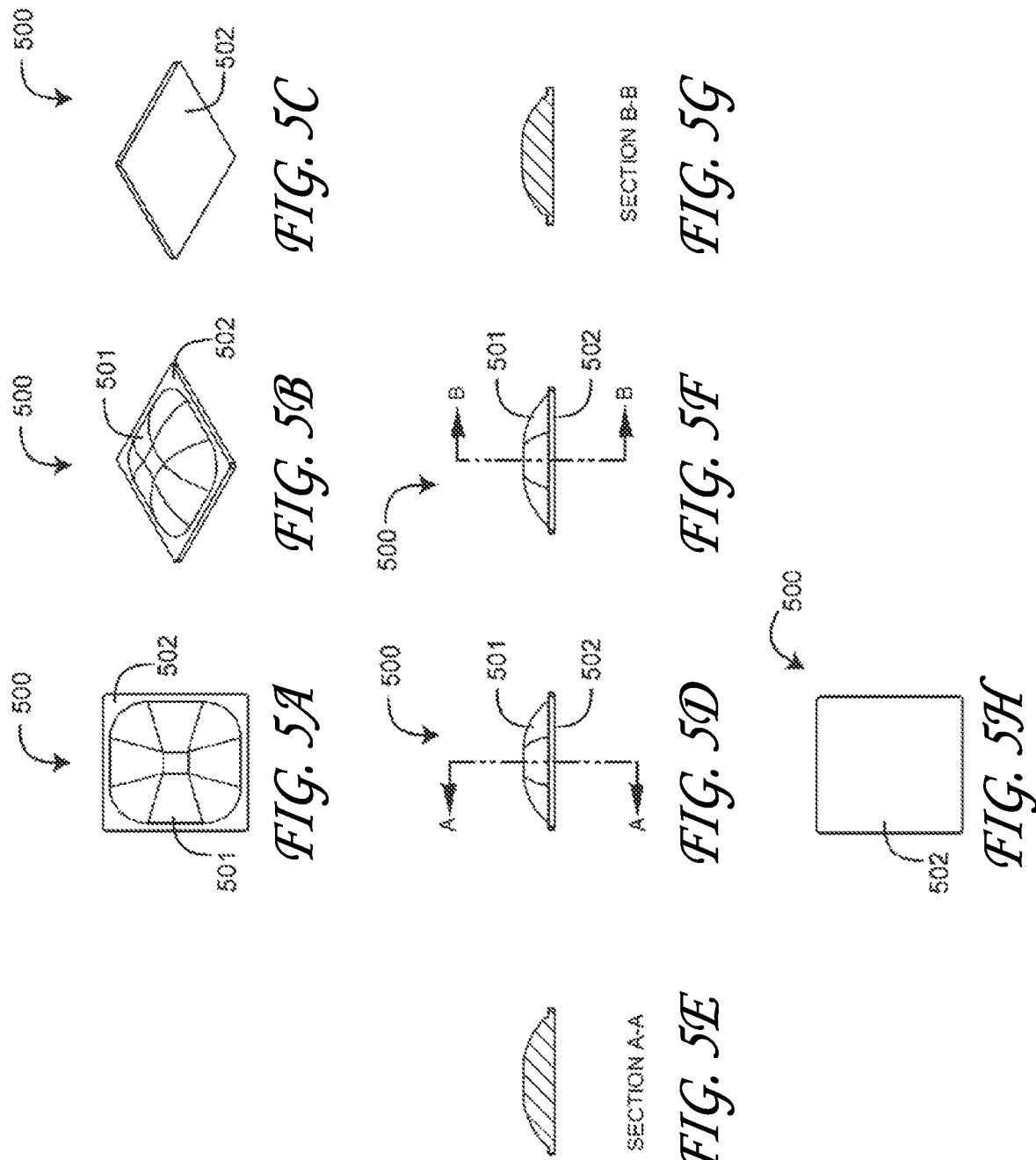
FIGS. 5A-H are a top plan view, top and bottom perspective views, first side and first side cross-sectional views, second side and second side cross-sectional views and a bottom view, respectively, of a near-field detector lens.
Figures 6A, 6B, 6C, 6D, 6E, 6F, 6G, 6H:
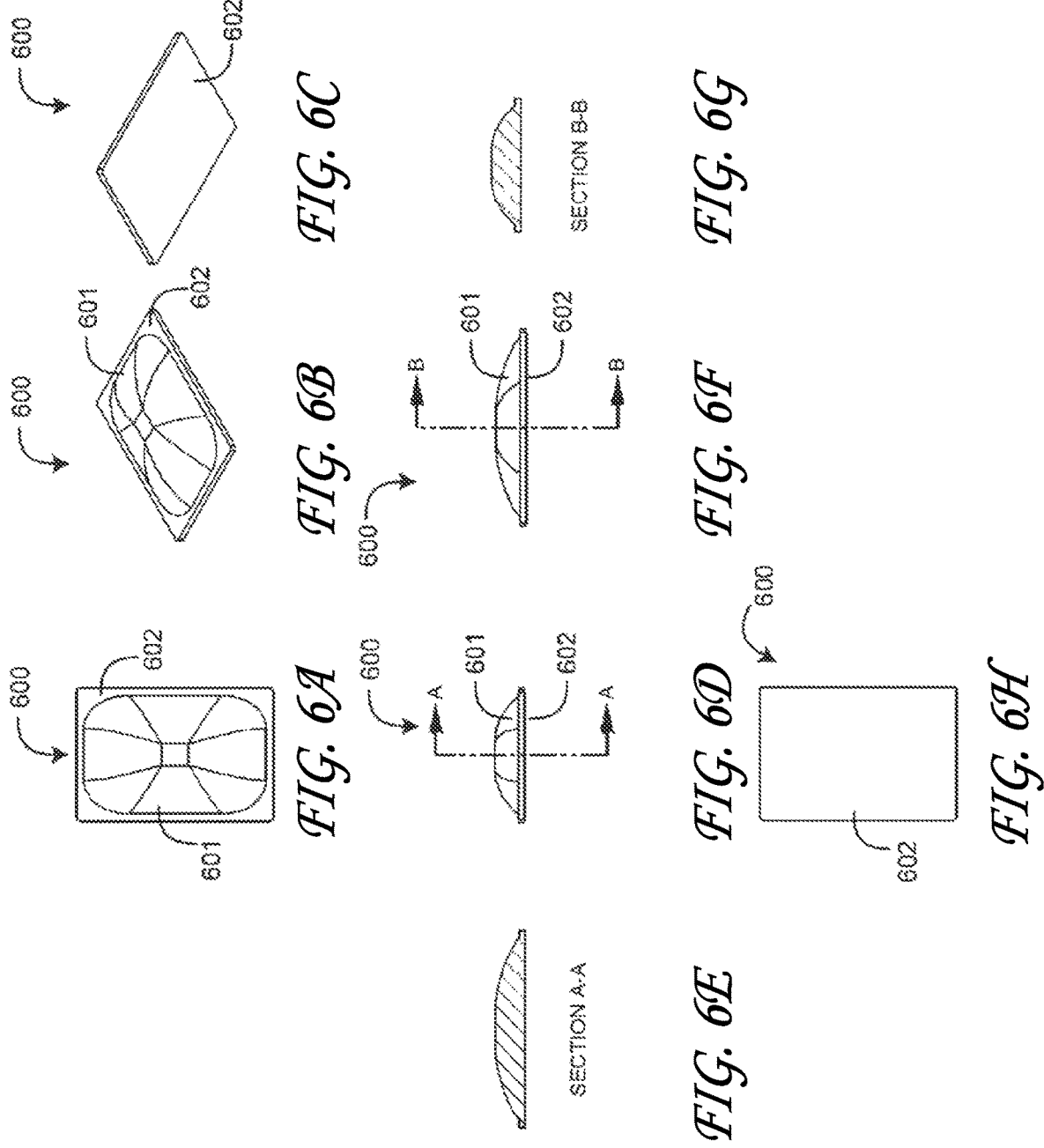
FIGS. 6A-H are a top plan view, top and bottom perspective views, first side and first side cross-sectional views, second side and second side cross-sectional views and a bottom view, respectively, of a far-field detector lens.

FIG. 4 illustrates sensor flex circuit 320 to sensor cable 330 interconnection. The flex circuit 320 is positioned on mounting pins in the top shell 360 (FIG. 3B). As shown in FIG. 4, cable 330 wires are soldered to flex circuit pads 410, 420. Cable 330 Kevlar bundles are wrapped around a shell post 430 for strain relief and secured with adhesive. A detector shield flap 440 is folded over detector wires soldered to the detector pads 410 and secured with Kapton tape. The base shell 370 (FIG. 3B) is then glued in place over the top shell 360 (FIG. 3B). In the embodiment of FIG. 4, the connections to the flex circuit 320 include four emitter anode conductors controlling four different wavelength emitters, a common emitter cathode conductor and an emitter shield, two near-field detector conductors, two far-field detector conductors and a detector shield. In an embodiment, the emitter and detector connections are physically separated between different circuit pads, for example, pads 410 and 420. This reduces and/or prevents cross talk and noise between the emitter lines and the detector lines. Of course a person of skill in the art will understand from the present disclosures that different numbers and types of connectors can be used with the presently described connection system.

FIGS. 5A-H illustrate an emitter lens and a near-field detector lens 500 having a generally half-dome focus element 501 and a generally rectangular, planar base 502. As described above, the lens base 502 is disposed over the flex-circuit-mounted emitter and near-field detector in order to focus emitted and detected light. Also as described above, the lens focus element 501 is configured to gently press into a tissue site when applied to the patient in order to maximize optical transmission via the skin surface. The focus elements can also use different three dimensional shapes as well in order to improve optical coupling with the skin and the present disclosure is not limited to the specific embodiments disclosed herein. For example, the lens can be spherical, cubed, rectangular, square, circular oblong or any other shape to increase optical transmission with the skin.

FIGS. 6A-H illustrate a far-field detector lens 600 having a generally oblong, half-dome focus element 601 and a generally oblong, planar base 602. As described above, the lens base 602 is disposed over the flex-circuit-mounted far-field detector so as focus detector received light. Also as described above, the lens focus element 601 gently presses into a tissue site in order to maximize optical transmission via the skin surface. Also, as described above with respect to FIG. 5, the present disclosure is not limited to the specific dimensions and shape described herein which are provided for illustrative purposes. Rather, as discussed above, the present disclose extends to other shapes and sizes of a focus element that will improve optical coupling. Moreover, the focus element 601 can comprise two or more different focus elements instead of a single larger focus element.

Figure 7:
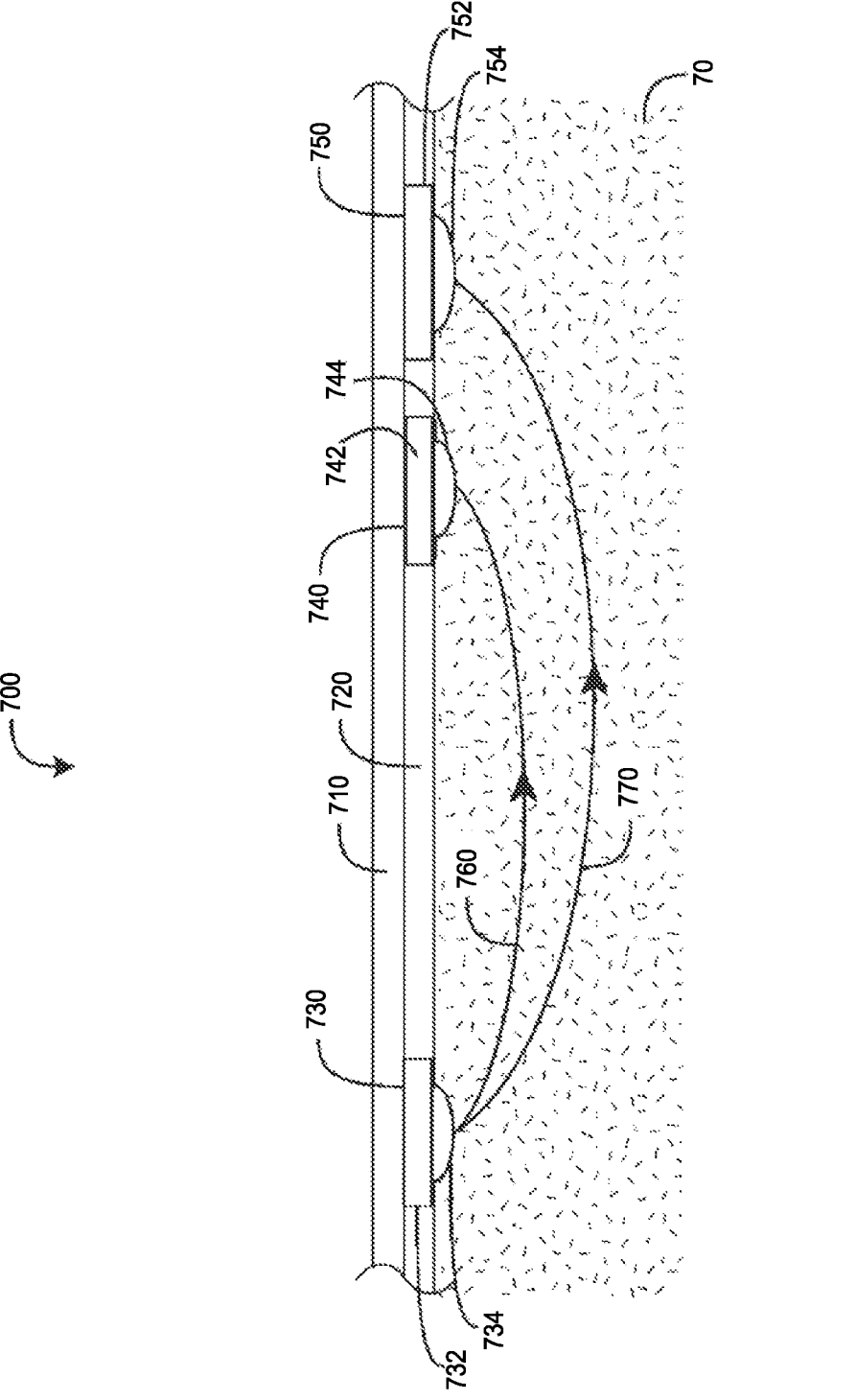
FIG. 7 is a cross-sectional view of a regional oximetry sensor attached to a tissue site and corresponding near-field and far-field emitter-to-detector optical paths.

FIG. 7 illustrates a regional oximetry sensor 700 attached to a tissue site 70 so as to generate near-field 760 and far-field 770 emitter-to-detector optical paths through the tissue site 70. The resulting detector signals are processed so as to calculate and display oxygen saturation ($SpO_2$), delta oxygen saturation ($\Delta SpO_2$) and regional oxygen saturation ($rSO_2$), as shown in FIG. 8C, below. The regional oximetry sensor 700 has a flex circuit layer 710, a tape layer 720, an emitter 730, a near-field detector 740 and a far-field detector 750. The emitter 730 and detectors 740, 750 are mechanically and electrically connected to the flex circuit 710. The tape layer 720 is disposed over and adheres to the flex circuit 710. Further, the tape layer 720 attaches the sensor 700 to the skin 70 surface.

As shown in FIG. 7, the emitter 730 has a substrate 732 mechanically and electrically connected to the flex circuit 710 and a lens 734 that extends from the tape layer 720. Similarly, each detector 740, 750 has a substrate 742, 752 and each has a lens 744, 754 that extends from the tape layer. In this manner, the lenses 734, 744, 754 press against the skin 70, advantageously increasing the optical transmission and reception of the emitter 730 and detectors 740, 750 through improved optical coupling. The lenses press into the skin and provide a more direct angle of light propagation through the skin between the emitter and detectors.

Figure 8B:
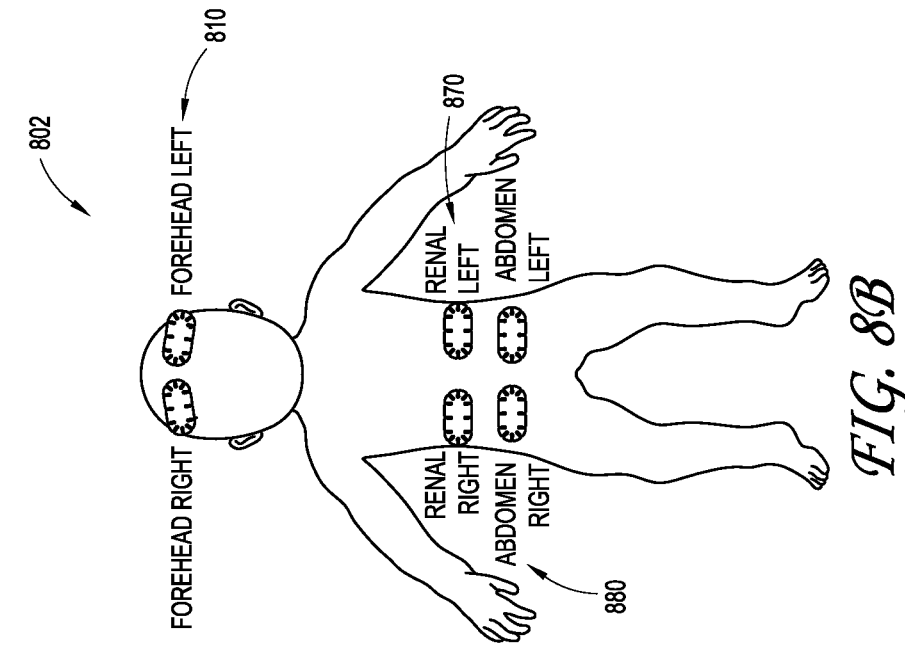
FIGS. 8A-B are a regional oximetry monitor display of sensor placement options for an adult and a child, respectively.
Figure 8A:
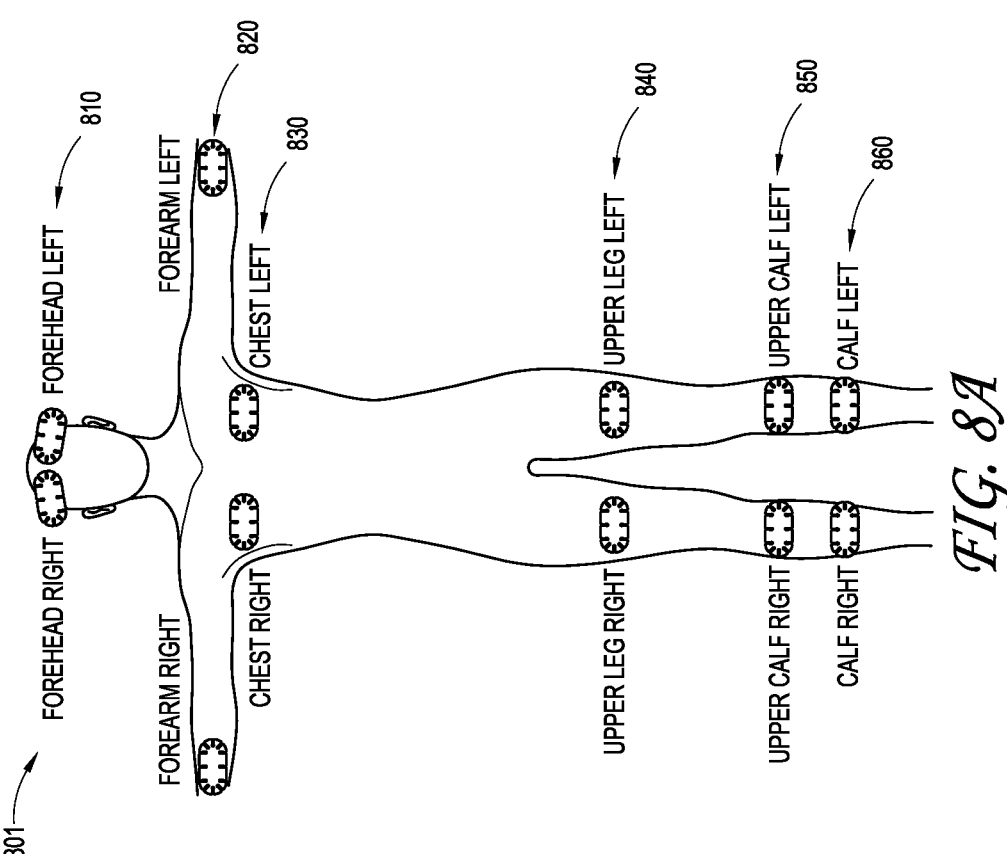
Figure 8C:
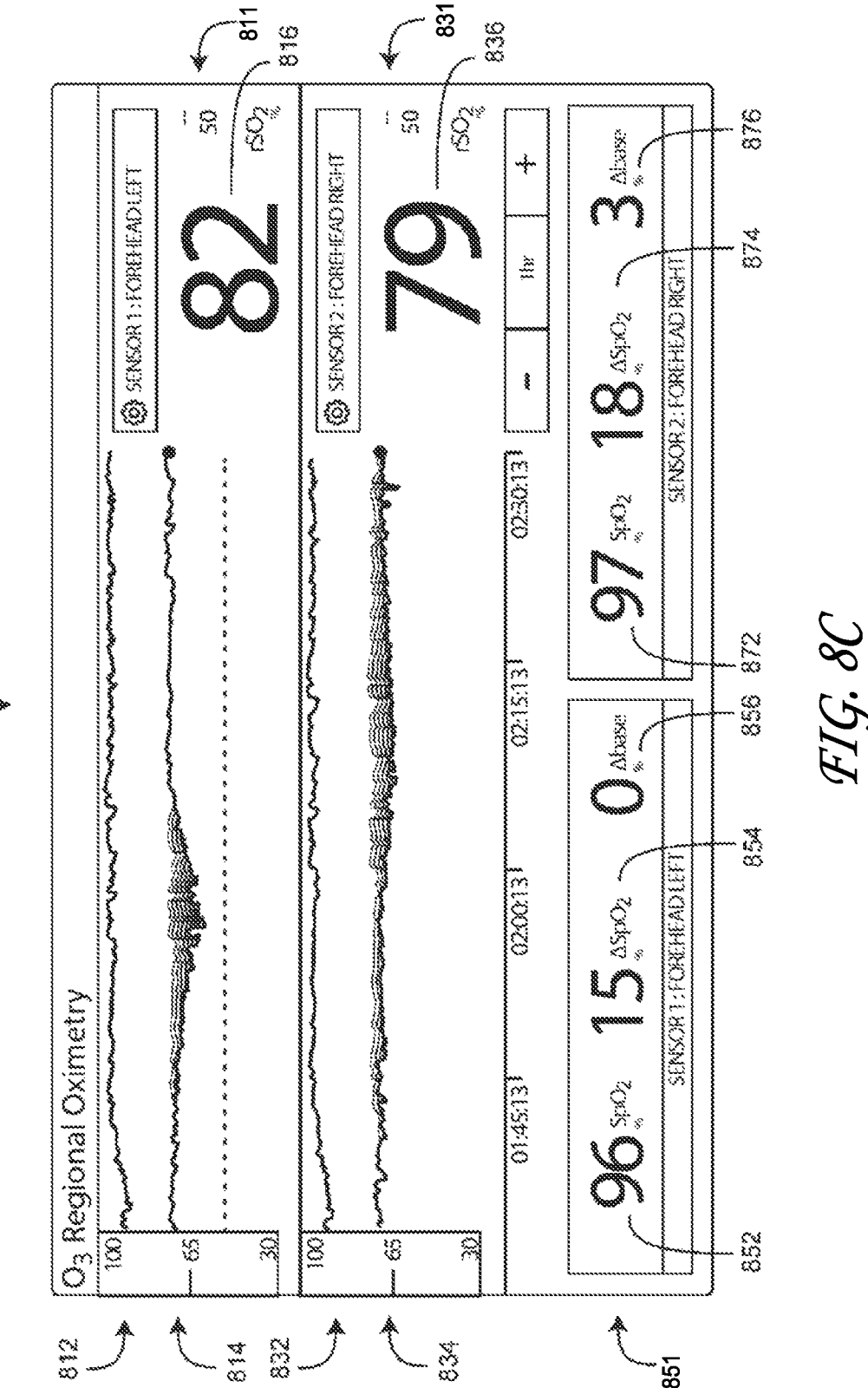
FIG. 8C is an exemplar regional oximetry monitor display using two regional sensors.

FIGS. 8A-B illustrate regional oximetry monitor embodiments for designating adult and child sensor placement sites. As shown in FIG. 8A, an adult form 801 is generated on a user interface display. Between one and four sensor sites can be designated on the adult form 801, including left and right forehead 810, forearm 820, chest 830, upper leg 840, upper calf 850 and calf 860 sites. Accordingly, between one and four sensors 200 (FIGS. 2A-C) can be located on these sites. A monitor in communication with these sensors then displays between one and four corresponding regional oximetry graphs and readouts, as described with respect to FIG. 8C, below. As illustrated in FIGS. 8A-8C, the sensor can be positioned on a patient so that the sensor stem 220 and attached cabling can extend radially out from the body on the various regional oximetry sensor sites. This configuration reduces patient discomfort by preventing wiring from crossing or crisscrossing over a patient face, torso or lower body. This configuration also reduces the potential for entanglement of wires from the multiple sensors and associated cabling.

As shown in FIG. 8B, a child form 802 is generated on a user interface display. Between one and four sensor sites can be designated on the child form 802, including left and right forehead 810, left and right renal 870, and left and right abdomen 880 sites. Any number of regional oximetry sensors can be deployed on a patient at the same time, but generally, between one and four sensors 200 (FIGS. 2A-C) are located on these sites at a given time. A monitor in communication with these sensors then displays between a corresponding regional oximetry graphs and readouts for each sensor, as described with respect to FIG. 8C, below. The displays of FIGS. 8A and 8B can also be selectively shown such that, for example, only an upper torso portion of the graphic is shown to prevent confusion by a care provider.

FIG. 8C illustrates a regional oximetry display 800 embodiment for monitoring parameters derived from between one and four regional oximetry sensors 200 (FIGS. 2A-C). This particular example is a two sensor display for monitoring, for example, a forehead left 811 site and a forehead right 831 site. In an upper display portion, the forehead left 812 site displays, for example, an $SPO_2$ graph 812, an $rSO_2$ graph 814 and an $rSO_2$ readout 816. Similarly, the forehead right 831 site displays, for example, an $SPO_2$ graph 832, an $rSO_2$ graph 834 and an $rSO_2$ readout 836.

Also shown in FIG. 8C, in a lower display portion, the forehead left 851 site displays, for example, an $SPO_2$ readout 852, a $\Delta SO_2$ readout 854 and a $\Delta_{base}$ readout 856. Similarly, the forehead right 830 site displays, for example, an $SPO_2$ readout 872, a $\Delta SO_2$ readout 874 and a $\Delta_{base}$ readout 876.

Figure 9A:
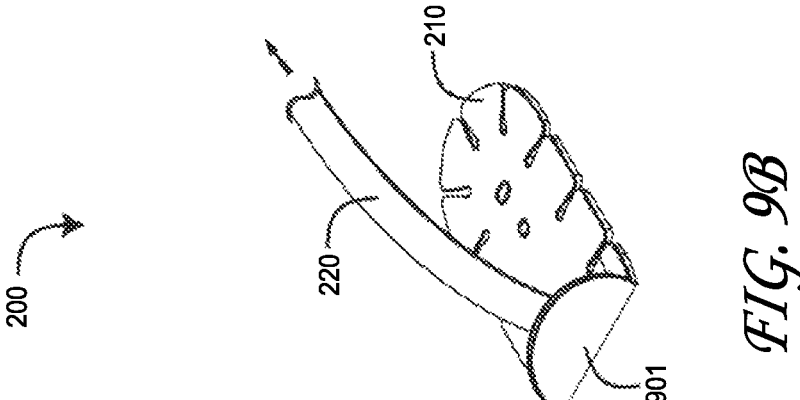
FIGS. 9A-B are top perspective views of a regional oximetry sensor being inadvertently peeled from a skin-surface monitoring-site due to a pulling force applied to the sensor stem and interconnecting sensor cable.
Figure 9B:
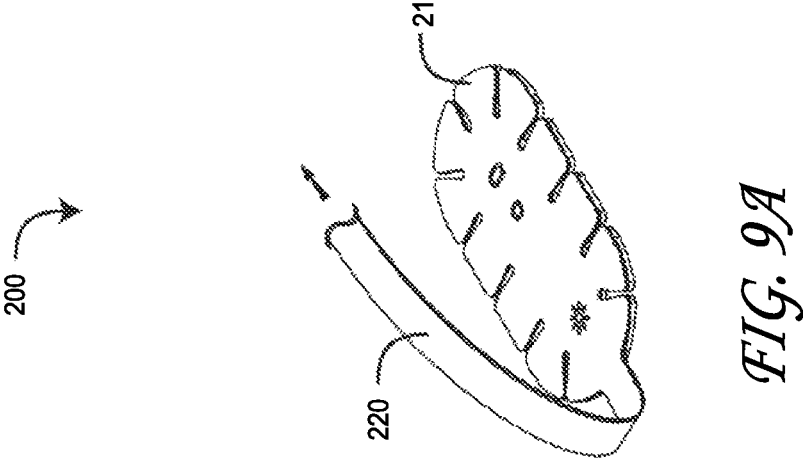

FIGS. 9A-B illustrate a problem that arises with a regional oximetry sensor 200 during use. The connector 250 is fixedly connected to a physiological monitor (not shown) that provides a read-out of parameters derived from the sensor 200. Patient movement away from the monitor may occur in a manner that pulls on the cable (not shown) and bends the attached stem 220 up and/or over the sensor head 210 (FIG. 9A). Continued patient movement away from the monitor may cause a portion of the sensor head 901 to peel off of the patient's skin (FIG. 2B), disrupting accurate parameter measurements. Indeed, continued patient movement may completely dislodge the sensor head 210 from the patient.

A peel-off resistant regional oximetry sensor has a sensor head attachable to a patient skin surface so as to transmit optical radiation into the skin and receive that optical radiation after attenuation by blood flow within the skin. A stem extending from the sensor head transmits electrical signals between the sensor head and an attached cable. The stem is terminated interior to the sensor head and away from a sensor head edge so as to define feet along either side of the stem distal the stem termination. The stem interior termination substantially transforming a peel load on a sensor head adhesive to less challenging tension and shear loads on the sensor head adhesive.

Figure 10:
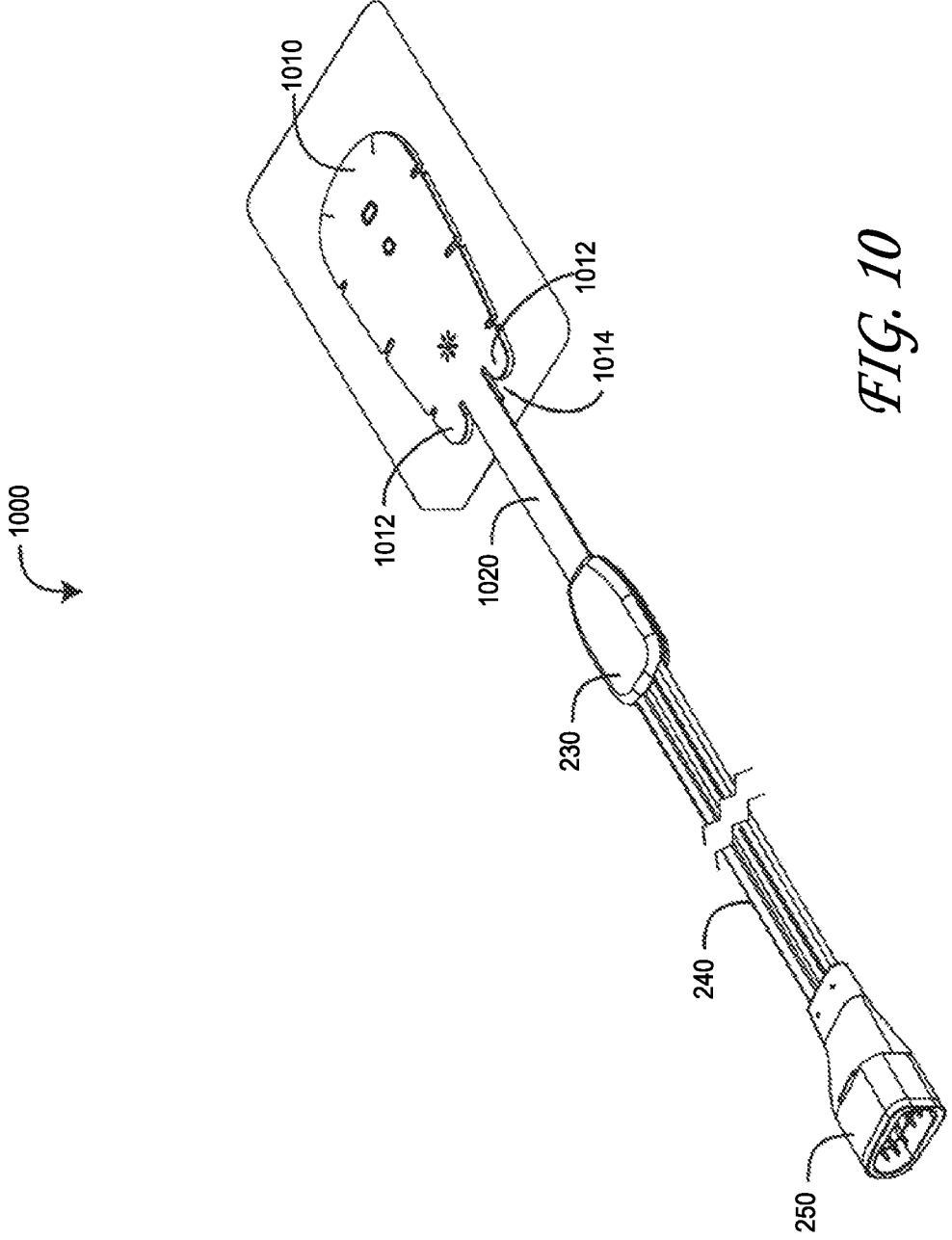
FIG. 10 is a top perspective view of a peel-off resistant regional oximetry sensor.

FIG. 10 illustrates an advantageous peel-off resistant regional oximetry sensor 1000 embodiment having a sensor head 1010, stem 1020, shell 230, cable 240 and connector 250. The sensor head 1010 houses an emitter, a near-field detector and a far-field detector within a layered tape having a top side and an adhesive bottom side disposed on a release liner, similar to that described with respect to FIGS. 2A-B, above. The peel-off resistant regional oximetry sensor 1000 has peel-resistant feet 1012 proximately disposed on either side of the stem. The feet are defined by stem slots 1014 separating the feet from the stem. This configuration advantageously moves the stem 1020 base from the edge of the sensor head (e.g. 210 FIG. 2A) to the interior of the sensor head 1010. As a result, potential peel loads on the sensor head adhesive resulting from the stem 1020 being pulled over the sensor head are substantially reduced, as described with respect to FIGS. 12A-13B, below.

Figure 11A:
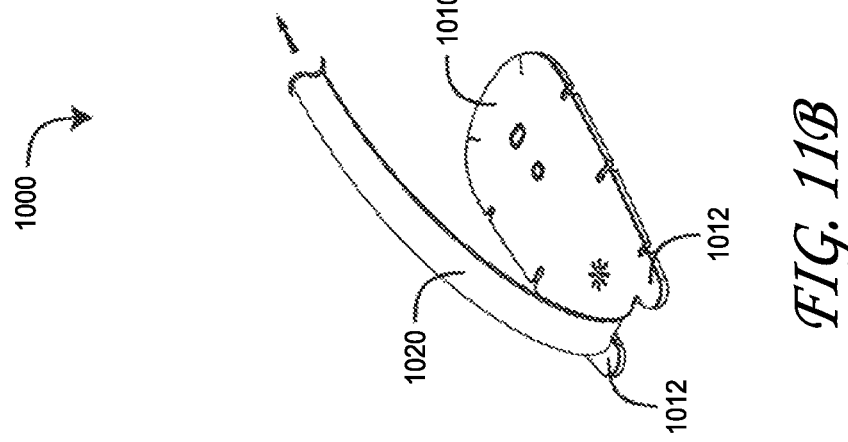
FIGS. 11A-B are top perspective views of a peel-off resistant regional oximetry sensor adhering to a skin-surface monitoring site despite a pulling force applied to the sensor stem and interconnecting sensor cable.
Figure 11B:
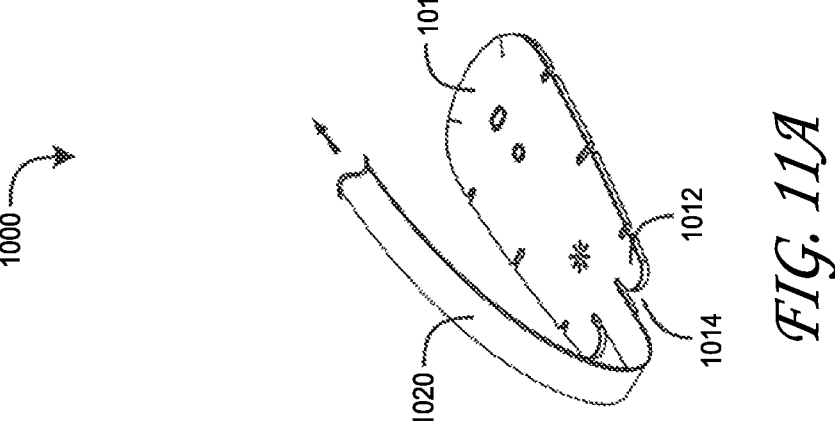

FIGS. 11A-B illustrate a peel-off resistant regional oximetry sensor 1000 adhering to a skin-surface monitoring site despite a pulling force applied to the sensor stem 1020 and interconnecting sensor cable. Patient movement relative to connected monitor tends to cause the stem 1020 to peel up the sensor head (see FIG. 2B, above). The sensor head feet 1012, however, advantageously extend away from the point where the stem 1020 begins applying a load to the sensor head adhesive, thus counteracting the peel away force. Further the resulting adhesive loads are different in kind and magnitude than the adhesive loads on the sensor head shown and described with respect to FIG. 2, above. Comparative adhesive loads are described in detail with respect to FIGS. 12A-13B, below.

FIGS. 12A-13B illustrate comparative adhesive loads applied to a regional oximetry sensor and a peel-off resistant regional oximetry sensor resulting from cable forces applied to the sensor head stems 220 (FIGS. 12A-B), 1020 (FIGS. 13A-B). As shown in FIGS. 12A-B, the stem 220 applies a substantial peel load 1221 to the sensor head 210 adhesive 1222, and the peel load 1221 is distributed over a relatively small area 1223 of the sensor head 210. It is well-know that a peel load 1221 is a substantial challenge to any adhesive, and the milder adhesives used on skin cannot easily overcome this challenge. As such, it is relatively easy for the sensor head 210 to become dislodged or completely detached from the patient.

As shown in FIGS. 13A-B, the stem 1020 applies different loads 1321 to the sensor head 310 adhesive 1322, 1323, 1324 than described with respect to FIGS. 12A-B. In particular, there is a marginal peel load on the adhesive as the result of the adhesive feet 1012 positioned opposite the connection point of the stem 1020 to the sensor head 1010. The sheer load due to the stem force 1321 is much less challenging to the feet adhesive 1024 compared to a peel load. Likewise, the tension load due to the stem force 1321 is less challenging to the feet adhesive 1322, 1323, compared to a peel load, and that tension load is distributed on both sides of the stem-to-head connection point. That is, the cumulative effect of positioning the stem 1020 somewhat to the interior of the sensor head 1010 and behind the feet 1012 is a greatly diminished adhesive peel load and much less challenging shear and tension loads distributed over a larger adhesive footprint. The advantageous result is a sensor head-to-cable stem interface that is much less likely to dislodge the sensor head from the patient when forces are applied to the sensor cable. Further, more skin-friendly adhesives can be utilized for sensor head attachment as a result of lowered adhesive loads.

A peel-off resistant regional oximetry sensor has been disclosed in detail in connection with various embodiments. These embodiments are disclosed by way of examples only and are not to limit the scope of this disclosure or the claims that follow. One of ordinary skill in art will appreciate many variations and modifications.

Terminology

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, engines, modules, circuits, and algorithm steps described in connection with the embodiments disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A regional oximetry sensor comprising:
   a sensor head comprising:
      a bottom surface configured to adhere the sensor head to skin of a subject at a measurement site;
      a top surface opposite the bottom surface and configured to face away from the skin when the regional oximetry sensor is in use; and
      a first end, a second end opposite the first end, a first side extending between the first and second ends, a second side extending between the first and second ends and opposite to the first side, a length extending between the first and second ends, and a width extending between the first and second sides, wherein the first end, the second end, the first side, and the second side form a perimeter of the sensor head, and wherein the second end comprises a rounded shape that curves outward from an interior of the sensor head, and wherein the width tapers along the length of the sensor head such that the first end is narrower than the second end;
   an emitter positioned at least partially within the sensor head and configured to transmit optical radiation toward the subject's skin, wherein the emitter is positioned closer to the first end of the sensor head than to the second end of the sensor head;

a first lens covering the emitter, the first lens protruding beyond the bottom surface of the sensor head and configured to press into the subject's skin when the sensor head is adhered to the subject's skin at the measurement site;
   a first detector and a second detector, each of the first and second detectors positioned at least partially within the sensor head and configured to receive at least a portion of the optical radiation after attenuation by blood flow within the subject's skin, wherein the first and second detectors are positioned closer to the second end of the sensor head than to the first end of the sensor head and closer to one another than to the emitter, and wherein the first detector, the second detector, and the emitter are aligned with one another along a longitudinal axis of the sensor head;
   a second lens covering the first detector and a third lens covering the second detector, the second and third lenses protruding beyond the bottom surface of the sensor head and configured to press into the subject's skin when the sensor head is adhered to the subject's skin at the measurement site; and
   a stem connected to the first end of the sensor head and configured to transmit electrical signals from the first and second detectors to a cable.

2. The regional oximetry sensor of claim 1, wherein the sensor head further comprises a plurality of tape layers.

3. The regional oximetry sensor of claim 2, wherein the plurality of tape layers at least partially encase the emitter and the first and second detectors.

4. The regional oximetry sensor of claim 2, further comprising a flexible circuit electrically connected to the emitter and the first and second detectors, wherein the flexible circuit is encased by the plurality of tape layers.

5. The regional oximetry sensor of claim 1, further comprising a plurality of indicators positioned on the top surface of the sensor head, each of the plurality of indicators aligned with one of the emitter, the first detector, and the second detector.

6. The regional oximetry sensor of claim 1, wherein each of the first lens, the second lens, and the third lens comprises a half-dome focus element and a planar base.

7. The regional oximetry sensor of claim 6, wherein:
   the planar base of each of the first lens and the second lens is square shaped;
   the planar base of the third lens is rectangular shaped; and
   the half-dome focus element of the third lens is oblong.

8. A regional oximetry sensor comprising:
   a sensor head comprising:
      a bottom surface configured to secure the sensor head to skin of a subject at a measurement site;
      a top surface opposite the bottom surface and configured to face away from the skin when the regional oximetry sensor is in use; and
      a first end, a second end opposite the first end, a first side extending between the first and second ends, a second side extending between the first and second ends and opposite to the first side, a length extending between the first and second ends, and a width extending between the first and second sides, wherein the first end, the second end, the first side, and the second side form a perimeter of the sensor head, and wherein the second end comprises a rounded shape that curves outward from an interior of the sensor head, and wherein the width tapers along the length of the sensor head such that the first end is narrower than the second end;

an emitter positioned at least partially within the sensor head and configured to transmit optical radiation toward the subject's skin, wherein the emitter is positioned closer to the first end of the sensor head than to the second end of the sensor head;

a first detector and a second detector, each of the first and second detectors positioned at least partially within the sensor head and configured to receive at least a portion of the optical radiation after attenuation by blood flow within the subject's skin, wherein the first and second detectors are positioned closer to the second end of the sensor head than to the first end of the sensor head; and a stem connected to the first end of the sensor head and configured to transmit electrical signals from the first and second detectors to a cable.

9. The regional oximetry sensor of claim 8, wherein the sensor head further comprises a plurality of tape layers.

10. The regional oximetry sensor of claim 9, wherein the plurality of tape layers at least partially encase the emitter and the first and second detectors.

11. The regional oximetry sensor of claim 9, further comprising a flexible circuit electrically connected to the emitter and the first and second detectors, wherein the flexible circuit is encased by the plurality of tape layers.

12. The regional oximetry sensor of claim 8, further comprising a plurality of indicators positioned on the top surface of the sensor head, each of the plurality of indicators aligned with one of the emitter, the first detector, and the second detector.

13. The regional oximetry sensor of claim 8, further comprising:

a first lens configured to be positioned between the emitter and the subject's skin when the sensor head is secured to the subject's skin, the first lens protruding beyond the bottom surface of the sensor head and configured to press into the subject's skin when the sensor head is secured to the subject's skin; and a second lens configured to be positioned between the first detector and the subject's skin when the sensor head is secured to the subject's skin; and a third lens configured to be positioned between the second detector and the subject's skin when the sensor head is secured to the subject's skin.

14. The regional oximetry sensor of claim 13, wherein each of the first lens, the second lens, and the third lens comprises a half-dome focus element and a planar base.

15. The regional oximetry sensor of claim 14, wherein:

the planar base of each of the first lens and the second lens is square shaped;

the planar base of the third lens is rectangular shaped; and the half-dome focus element of the third lens is oblong.

16. The regional oximetry sensor of claim 8, wherein the first and second detectors are positioned closer to one another than to the emitter, and wherein the first detector, the second detector, and the emitter are aligned with one another along a longitudinal axis of the sensor head.

17. A regional oximetry sensor comprising:

a sensor head comprising:

a bottom surface configured to secure the sensor head to skin of a subject;

a top surface opposite the bottom surface; and a first end, a second end opposite the first end, a first side, a second side, a length extending between the first and second ends, and a width extending between the first and second sides, and wherein the second end comprises a rounded shape and wherein the width tapers along the length of the sensor head such that the first end is narrower than the second end;

an emitter positioned at least partially within the sensor head and configured to transmit optical radiation toward the subject's skin;

at least one detector an positioned at least partially within the sensor head and configured to receive at least a portion of the optical radiation after attenuation by blood flow within the subject's skin; and a stem connected to the first end of the sensor head and configured to transmit electrical signals from the first and second detectors to a cable.

18. The regional oximetry sensor of claim 17, further comprising a plurality of indicators positioned on the top surface of the sensor head, each of the plurality of indicators aligned with one of the emitter and the at least one detector.

19. The regional oximetry sensor of claim 17, wherein:

the emitter is positioned closer to the first end of the sensor head than to the second end of the sensor head;

the at least one detector comprises a first detector and a second detector; and the first and second detectors are positioned closer to the second end of the sensor head than to the first end of the sensor head and closer to one another than to the emitter.

20. The regional oximetry sensor of claim 19, wherein the first detector, the second detector, and the emitter are aligned with one another along a longitudinal axis of the sensor head.

* * * * *